(12) United States Patent
Keplinger et al.

(10) Patent No.: US 7,238,374 B2
(45) Date of Patent: Jul. 3, 2007

(54) PROCESS AND SUBSTANCES FOR THE RELEASE OF A GROWTH-REGULATING FACTOR FROM ENDOTHELIAL CELLS

(76) Inventors: Klaus Keplinger, Mullerstrasse 30, A-6020 Innsbruck (AT); Martin Wurm, Speckbacherstrasse 27, A-6020 Innsbruck (AT); Gerhard Laus, Innrain 100, A-6020 Innsbruck (AT)

( * ) Notice: Subject to any disclaimer, the term of this patent is extended or adjusted under 35 U.S.C. 154(b) by 0 days.

(21) Appl. No.: 09/788,888

(22) Filed: Feb. 20, 2001

(65) Prior Publication Data

US 2002/0039790 A1 Apr. 4, 2002

Related U.S. Application Data

(63) Continuation-in-part of application No. 09/341,607, filed on Oct. 21, 1999, now abandoned, which is a continuation of application No. PCT/AT98/00008, filed on Jan. 20, 1998.

(51) Int. Cl.
*A61N 45/00* (2006.01)
*A61N 43/16* (2006.01)
*C07G 5/00* (2006.01)
*C08L 97/00* (2006.01)

(52) U.S. Cl. .................. 424/725; 530/502; 514/411; 514/454

(58) Field of Classification Search ............ 514/411, 514/454, 885; 530/502
See application file for complete search history.

(56) References Cited

U.S. PATENT DOCUMENTS 4,844,901 A * 7/1989 Keplinger et al.
5,302,611 A * 4/1994 Keplinger et al.
5,723,625 A * 3/1998 Keplinger et al.

FOREIGN PATENT DOCUMENTS

| DE | B 118 4897 | 1/1962 |
| EP | 0 665 231 A1 | 1/1994 |
| GB | 1056537 | 1/1967 |
| GB | 1056863 | 2/1967 |
| JP | 03016695 | 2/1991 |
| JP | 04118580 | 5/1992 |
| WO | WO 82/01130 | 4/1982 |
| WO | WO 86/00524 | 1/1986 |
| WO | WO 90/13027 | 11/1990 |
| WO | WO 91/09035 | 6/1991 |
| WO | WO 95/21169 | 8/1995 |

OTHER PUBLICATIONS

Raymond–Hamet et al. Academies des Sciences, Seance du 8 Septembre 1952, 547–550.
Chau et al. (1966) Alkaloids of Uncaria pteropoda. Isolation and structures of pteropodine and Isopteropodine. J. Chem. Soc. 1966, 2245–2249.
Johns et al. (1966) Uncaria alkaloids. two stereoisomers of mitraphylline from Uncaria bernysii and U. ferrea. Tetrahedron Letters 40, 4883–4888.
Becham et al. (1967) The stereochemistry of oxindole alkaloids, uncarines A, B (formasine), C (pteropodine), D (speciophylline), E (Isopteropodine) and F. Aust. J. Chem. 21, 491–504.
Hart et al. (1967) Uncarine C, D (Speciophylline), E, and F: C–3 and C–7 epimeric oxindoles related to tetrahydroalstonine. Chem. Comm. 2, 87–88.
Chan, K.C.. (1968) Gambirdine and Isogambridine. the alkaloids from Uncaria gamir (Hunt.) ROXB. Tetrahedron Letters 30, 3403–3406.
Merlini et al. (1972) Indole alkaloids from Uncaria gambir. Phytochemistry 11, 1525–1526.
Phillipson et al. (1973) Alkaloids of Uncaria longiflora. Phytochemistry 12, 2791–2794.
Phillipson et al. (1973) Indole and oxindole alkaloids from Uncaria bernaysia. Phytochemistry 12, 1481–1487.
Phillipson et al. (1973) Oxindole alkaloids from Uncaria macrophylia. Phytochemistry 12, 2795–2798.
Hemingway et al. (1974) Alkaloids from S. America species of Uncaria (Rubicaeae). J. Pharm. Pharmacol. 26, 113 P.
Phillipson et al. (1974) Augustine and related alkaloids from species of Mitragnya, Nauclea, Uncaria and Strychnos. Phytochemistry 13, 973–978.
Montengro de Matta, S. (1975) Alkaloids and proclanidins of an Uncaria Sp. from Peru. II Farmaco 31, 527–535.
Nozoye et al. (1975) Studies on Uncaria alkaloid. XXI Separation of Rhynchophylline and corynoxeine. Journal of the Pharmaceutical Society of Japan 95, 758–759.
Phillipson et al. (1975) Alkaloids of Uncaria attenuate, U. orientalis and U. canescens. Phytochemistry 14, 1855–1863.
Phillipson et al. (1975) Chromatographic and spectroscopic methods for the Identification of alkaloids from Herbarium samples of the genus Uncaria. J. of Chromatography 105, 163–178.
Almi, N.; Yamanaka, E.; Shinma, N.; Fjiu, M.; Kurita, J.; Sakai, S.; Haginiwa, J. (1977) Studies on plants containing indole alkaloids. VI. Minor bases of Uncaria rhynchophylia Mlq. Chemical Pharmaceutical Bulletin 25, 2067–2071.

(Continued)

*Primary Examiner*—Christina Chan
*Assistant Examiner*—Phuong N. Huynh
(74) *Attorney, Agent, or Firm*—Laurence A. Greenberg; Werner H. Stemer; Ralph E. Locher

(57) ABSTRACT

Endothelial cells have the natural property of releasing soluble factors into the fluid surrounding them, said factors altering the behavior of immune cells. In cell systems containing at least endothelial cells, the release of this type of factor, which promotes the proliferation of resting and weakly activated lymphocytes and at the same time inhibits the proliferation of highly activated lymphocytes and transformed lymphoblasts without impairing their other vital functions, is induced by administration of pentacyclic oxindole alkaloids but inhibited by the concurrent administration of tetracyclic oxindole alkaloids.

8 Claims, 5 Drawing Sheets

OTHER PUBLICATIONS

Figure 1:
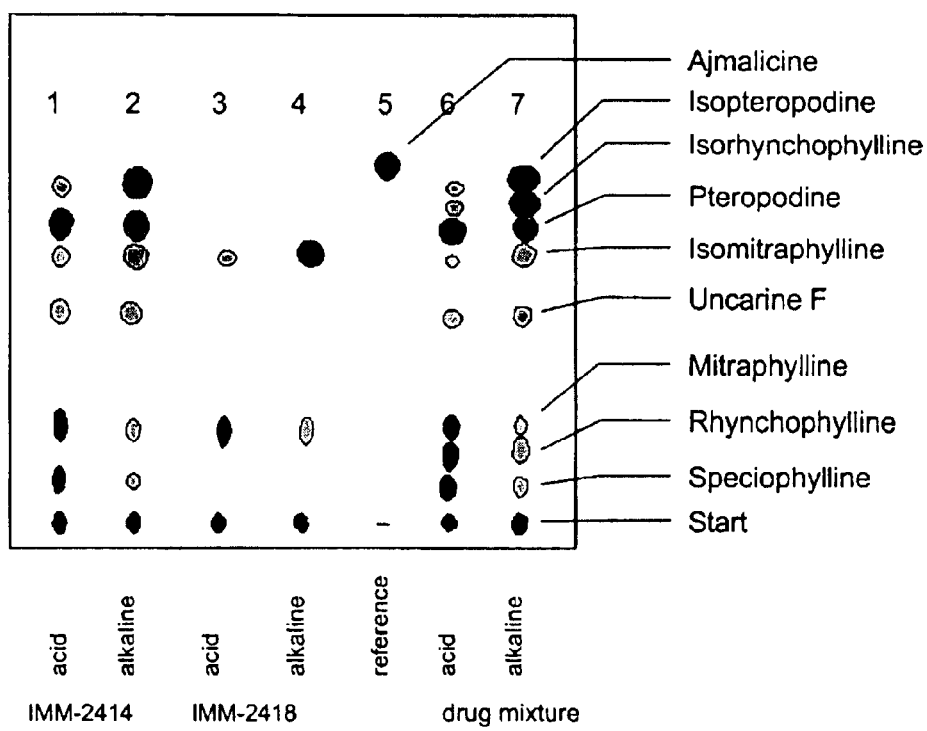

Ponglux, G., Tantivatana, P., Pummangura, S. (1977) Alkaloids from the leaves of Uncaria homomalia. Planta Medica 31, 26–30.

Herat et al. (1978) Alkaloids and other constituents f Uncaria eliptica nad Canthium dioccum. Phytochemistry 18, 1385–1387.

Herath, W.H.M.W., Sultanbawa, M.U.S., Wannigama, G.P. (1978) Chemical Investigation of Ceylonese plants. Part 33. Three new ursene carboxylic acids from Uncaria thwaltesil. Phytochemistry 17, 1979–1981.

Tantivatana, P., Ponglux, D., Jirawongse, V., Silpvisavanont, Y. (1979) Alkaloids from Uncaria quadrangularis. Planta Medica 35, 92–94.

Tantivatana, P., Ponglux, D., Wongseripiptana S., Phillipson, J.D. (1980) Alkaloids of Uncaria. Part 7. Alkaloids of U. attenuate (U. salacceusis) from N.E. Thailand. Planta Medica 40, 299–301.

Almi, N., Shito, T., Fukushima, K., Ital, Y., Aoyama, C., Kunisawa, K., Sakai, S., Haginiwa, J., Yamasaki, K. (1982) Studies on plants containing indole alkaloids. VIII. Indole alkaloid glycosides and other constituents of the leaves of Uncaria rhynchophylia Miq. Chemical Pharmaceutical Bulletin 30, 4046–4051/

Phillipson et al. (1982) Separation of heteroyohimbine and oxindole alkaloids by reversed–phase high–performance liquid chromatography. Journla of Chromatography 244, 91–98.

Lavault, M., Moretti, C., Bruneton, J. (1983) Alkaloids of Uncaria gulanensis. Planta Medica 47, 244–245.

Phillipson, J.D., Supavita, N. (1983) Alkaloids from Uncaria species. Part 8. Alkaloids of Uncaria elliptica. Phytochemistry 22, 1809–1813.

Yamanaka, E., Kimizuka, Y., Aimi, N., Sakai, S., Haginiwa, J. (1983) Studies of plants containing indole alkaloids. IX. Determination of tertiary alkaloids in various parts of Uncaria rhynchophylla Miq. Journal of the Pharmaceutical Society of Japan 103, 1028–1033.

Kanatani, H., Kohda, H., Yamasaki, K., Hotta, I., Nakata, Y., Segawa, T., Yamanaka, E., Aimi, N., Sakai, S. (1985) The active principles of the branchlet and hook of Uncaria sinensis Ollv. examined with a 5–hydroxytryptamine receptor binding assay. Journal of Pharmacy and Pharmacology 37, 401–404.

Wagner, H., Kreutzkamp, B., Jurcic, K. (1985) Alkaloids from Uncaria tomentosa and their phagocytosis enhancement effect Planta Medica 419–423.

Kawazoe et al. (1987) Cultivation and breeding of Uncaria rhynchophylla. Journal of Pharmaceutical Science 76, 203P.

Ponglux, D., Wongserlpipatana, S., Aimi, N., Nishimura, M., Ishikawa, M., Sada, H., Haginiwa, J., Sakai, S. (1990) Structure and synthesis of two new types of exindole alkaloids from Uncaria salacensis. Chemical Pharmaceutical Bulletin 38, 573–575.

Kam, T.S., Lee, K.H., Goh, S.H., (1991) Studies on Malaysian Uncaria. Part 4. Dimeric indole alkaloids from Uncaria callophyllia. Phytochemistry 30, 3441–3444.

Arbain, D., Byrne, L.T., Putra, M.M., Sargent, M.V., Syarif, M. (1972) A new glucoalkaloid from Uncaria glabrata. Journal of the Chemical Society, Perkin Transactions 1 665–666.

Kam, T., Lee, K.H., Goh, S.H. (1992) Studies on Malaysian Uncaria. 5. Alkaloid distribution in Malaysian Uncaria. Phytochemistry 31, 2031–2034.

Kawazoe, S., Kobayashi, S., Mizukami, H., Ohashi, H. (1992) Effect of soil moisture content on growth, crude drug "Cho–to–ko" yield, and oxindole alkaloid content of Uncaria rhynchophylla. Sci. Rep. Kyoto Prefectural University 43, 31–34.

Stuppner et al. HPLC–Analyse der Oxindolalkaloide aus Uncaria tomentosa. Scientia Pharmaceutica 60, 168P.

Stuppner, H., Sturm, S., Konwalinka, G. (1992a) Capillary electrophoretic analysis of oxindole alkaloid from Uncaria tomentosa. Journal of Chromatography 609, 375–380.

Strippner, H., Sturm, S., Konwalink, G. (1992b) HPLC analysis for the main oxindole alkaloids from Uncaria tomentosa. Chromatographia 34, 597–600.

Arbain et al. (1993) The Alkaloids of Uncaria glabrata. Aust. J. Chem. 46, 863–872.

Liu, H., Feng, X. –(1993) Oxindole alkaloids from Uncaria sinensis. Phytochemistry 33, 707–710.

Seki et al. (1993) A nuclear magnetic resonance study on the eleven steroisomers of Heteroyohimbine–type oxindole alkaloids. Chem. Pharm. Bull 41, 2077–2086.

Stuppner, H., Sturm, S., Gelsen, G., Zillan, U., Konwalinka, G. (1993) A differential sensitivity of oxindole alkaloids to normal and leukemic cell lines. Planta Medica 59, Supplement, A 583.

Laus, g., Keplinger, D. (1994) Separation of stereoisomeric oxindole alkaloids from Uncaria tomentosa by high performance liquid chromatography. Journal of Chromatography A 662, 243–249.

Wu, T., Chan, Y. (1994) Constituents of leaves of Uncaria hirsuta Haviland. Journal of the Chinese Chemical Society 41, 209–212.

Laus, G., Teppner, H. (1996) The alkaloids of an Uncaria rhynchophlia (Rublaceae–Coptosapelteae). Phyton (Austria) 36, 185–196.

Tirillini, B. (1996 Fingerprints of Uncaria tomentosa leaf, stem and root bark decoction. Phytherapy Research 10, 67–68.

van Ginkel, A.(1996) Identification of the alkaloids and flavanoids from Uncaria tomentosa bark by TLC in quality control. Phytotherapy Research 10, 18–19.

Aimi, N., Shimizu, T., Sada, H., Takayama, H., Sakai, S., Wongseripipatana, S., Ponglux, D. (1997) Structures of Us–7 and Us–8: a new type of oxindole alkaloids isolated from Uncaria attentata Korth. Journal of the Chemical Society, Perkin Transactions 1 187–188.

Diyabalanage, T.K.K., Kumaribamy, B.M.M., Wannigama, G.P., Jayasinghe, L., Merlin, L., Seaglioni, L. (19970 Alkaloids of Uncaria elliptica. Phytochemistry 45, 1731–1732.

Lopex–Avilla et al. Supercritical fluid extraction of oxindole alkaloids from Uncaria tomentosa. J. High Resol. Chromatogr. 20, 231–236.

Laus et al. (1997), Alkaloids of Peruvian Uncaria tomentosa. Phytochemistry 45, 855–860.

Reinhard K.H., Uncaria tomentosa (Willd.)DC–Cat's Claw, Una de gato oder Katzenkralle. Portrait einer Arzneipflanze. Zeitschrift fü Phytotherapie 18, 112–121, 1997.

Arbain, D., Afrida, Ibrahim, S., Sargent, M. V., Skelton, B. W., White, A. H. (1998) The alkaloids of Uncaria of glabrata. Australian Journal of Chemistry 51, 961–964.

Sakakibara, I., Takahashi, H., Terabayashi, S., Yuzuribara, M., Kubo, M., Ishige, A., Higuchi, M., Komatsu, Y., Okada, M., Maruno, M., Biqiang, C., Jiang, H. X. (1998) Effect of oxindole alkaloids from the books of Uncaria macrophylia on thiopental–induced hypnosis. Phytomedicine 5, 83–86.

Wurm, M., Kacani, L., Laus, G., Keplinger, K., Dierich, M.P. (1998) Pentacyclic oxindole alkaloids from Uncaria tomentosa induce human endothelial cells to release a lymphocyte–proliferation–regulating factor. Planta Medica 64, 701–704.

Keplinger, K., Laus, G., Wurm, M., Dierich, M.P., Teppner, H. (1999) Uncaria tomentosa (Willd.) DC.–Ethnomedicinal use and new pharmacological, toxicological and botanical results. Journal of Ethnopharmacology 64, 23–34.

Lee, K.K., Zhou, B.–N., Kingston, D.G.I., Valsberg, A.J., Hammond, G.B. (1999) Bioactive Indole alkaloids from the bark of Uncaria gulanensis. Planta Medica 65, 759–760.

Lemair, I., Assinewe, V., Cano, P., Awang, D.V.C., Aruason, J.T. (1999) Stimulation of Interleukin–1 and –6 production in alveolar macrophages by the neotropical llana, Uncaria tomentosa (Ufia de Gato). Journal of Ethnopharmacology 64, 109,115.

Masumiya, H., Saitoh, T., Tanaka, Y., Horle, S., Aimi, N., Takayama, H., Tanaka, H., Shigenobu, K. (1999) Effects of hirsutine and dihydrocorynantheine on the action potentials of sino–atrial node, atrium and ventricle. Life Sciences 65, 2333–2341.

Reinhard, K. H. (1999) Uncaria tomentosa (Willd.) D.C.: cat's claw, una de gato, or saventaro. Journal of Alternative and Complementary Medicine 5, 143–151.

Sakakibara, I., Terabayashi, S., Kubo, M., Higuchi, M., Komatsu, Y., Okada, M., Taki, K., Kamei, J. (1999) Effect on locomotion of Indole alkaloids from the hooks of Uncaria plants. Phytomedicine 6, 163–168.

Kitajima, M., Hashimoto, K.–I., Yokoya, M., Takayama, H., Aimi, N., Sakai, S. (2000b) A new gluco indole alkaloid, 3, 4–dehydro–5–carboxystrictosidine, from Peruvian Una de Gato (Uncaria tomentosa). Chemical Pharmaceutical Bulletin 48, 1410–1412.

Sheng, Y., Peru, R.W., Wagner, H. (2000b) Treatment of chemotherapy–induced leukopenia in a rat model with aqueous extract from Uncaria tomentosa. Phytomedicine 7, 137–143.

Song, C., Fan, Y., Huang, W., Wu, D., Hu, Z. (2000) Different hypotensive effects of various active constituents isolated from Uncaria rhynchophylla. Chinese Traditional Herbal Drugs 31, 762–764.

Ganzera, M., Muhammad, I., Khan, I.A. (2001) Improved method for the determination of oxindole alkaloids in Uncaria tomentosa by high performance liquid chromatography. Planta Medica 67, 447–450.

Muhammad, I., Dunbar, D.C., Khan, R.A., Ganzera, M., Khan, I.A. (2001) Investigation of Ufia De Gato. 7–Deoxyloganic acid and 15N NMR spectroscopic studies on pentacyclic oxindole alkaloids from Uncaria tomentosa. Phytochemistry 57, 781–785.

Muhammad, I., Khan, I. A., Fischer, N. H., Fronczek, F. R. (2001) Two sterolsomeric pentacyclic oxindole alkaloids from Uncaria tomentosa: uncarine c and uncarine E. acta Crystallographica C 57, 480–482.

Pengsuparp, T., Indra, B., Nakagawasai, O., Tadano, T., Mimaki, Y., Sahida, Y., Ohizumi, Y., Kisara, K. (2001) Pharmacological studies of gelssoschizine methyl ether, isolated from Uncaria sinensis Oliv., in the central nervous system. European Journal of Pharmacology 425, 211–218.

Tao, C., YI, Y., Xu, Q. (2001) Studies on chemical constituents of uncaria yunanensis Hsia.C.C. Acta Pharmaceutica Sinica 36, 120–122.

Aguilar, J.L., Rojas, P., Marccio, A., Plaza, A., Baner, R., Reininger, E., Klaas, C.A., Merfort, I. (2002) AntiInflammatory activity of two different extracts of Uncaria tomentosa (Rubiaceae). Journal of Ethnopharmacology 81, 271–276.

Kang, T.–H., Matsumoto, K., Tohda, M., Murakami, Y., Takayama, H., Kitajima, M., Aimi, N., Watanabe, H. (2002) Pteropodine and isoteropodine positively modulate the function of rat muscarinic M1 and 5–HT2 receptors expressed in Xenopus oocyte. European Journal of Pharmacology 444, 39–45.

Laus, g., Wurst, K. (2002) X–Ray Crystal Structure Analysis of Oxindole Alkaloids. Helv. Chim. Aeta 86, 181–187.

Mur, E., Hartig, F., Eibl, G., Schirmer, M. (2002) Randomized double blind trial of an extract from the pentacyclic alkaloid–chemotype of Uncaria tomentosa for the treatment of rheumatoid arthritis. Journal of Rheumatology 29, 678–681.

Sandovil, M., Okuhama, N.N., Zhang, X.–J., Condezo, L.A., Lao, J., Angeles, F.M., Musah, R.A. Bobrowski, P., Miller, M.J.S. (2002) AntiInflammatory and antioxidant activities of cat's claw (Uncaria tomentosa and Uncaria guianensis) are independent of their alkaloid content. Phytomedicine 9, 325–337.

Yuzurihara et al. (2002) Geissoschizine methyl ether, and indole alkaloid extracted from Uncariae Ramulus et Uncus, is a potent vasorelaxant of isolated rat aorta. European Journal of Pharmacology 444, 183–189.

Jing–Shan et al. (2003) Pharmagological actions of Uncaria alkaloids, rhynchophylline and isohynchophylline. Aeta Pharmacol Sin 24, 97–101.

Chan, K. C. (1969) The stereochemistry of pteropodine and isoteropodine; Phytochemistry 8, 219–222.

Ban et al. (1974) The synthesis of 3–spirooxindole derivatives. Tetrahedron Letters No. 2, 187–190.

Titeux et al. (1975) Structure des caboxines: alcaloides oxindoliques dyu cabucala fasciculata, Phytochemistry 14, 565–568.

Brown et al. (1976) A novel synthesis of isohynchophylline and rhynchophIlline from sceologanin, Tetrahedron Letters No. 17, 1401–1402.

Masatoshi et al. (1976) Effect of Indole alkaloids from Gardenia genus and Uncaria genus of neuromuscular transmission in the rat limb in situ, Chemical Abstracts 84, abstract 144859u.

Sharipov et al. (1976) Alkanoids of Vinca erecta, Chemistry of Natural Compounds 12/3, 355–356.

Chkhikadze et al. (1976) Structure of herboxine, Chemistry of Natural Compounds 12/2, 201–202.

Phillipson et al. (1978), Alkaloids of Uncaria, Lloydia 41/6, pages 503/570.

Majumder et al. (1978) Stereochemistry and relative stability of the oxindoles derived from venenatine and alstovenine, Tetrahedron Letters 34, 3341–3344.

Chang et al. (1979) Study on the antihypertensive action of uncarine A an alkaloid of Uncaria formosana used in Chinese herb medicine, chemical Abstracts 1–Pharamadynamics 91, abstract 102109p.

Chang et al. (1979) Study on the mode of hypotensive action of Uncaria A, Chemical Abstracts 1–Pharmacodynamics 90, abstracts 115313e.

Harada et al. (1979) Effects of Indole alkaloids from Gardenia nutans Sieb. and Zucc. and Uncaria rhynchorphylla Miq. on a guinea pig urinary bladder preparation in situ, Chemical Abstracts 1–Pharmacodynamics 91, abstract 49608x.

Chang et al. (1980) Hypotensive effect of rhynchophylla total alkaloids and rhynchophylline, Chemical Abstracts 1–Pharmacodynamics 92, abstract 191363c.

Castillo et al. (1982) Flora salvadorena, Anales de Quimica 78, 180–183.

Chan et al (1986) Alkaloids of Uncaria pteropoda, Isolation and structures of pteropodine and isopteropodine, Journal of the Chemical Society, Section C, Organic Chemistry, 2245–2249.

* cited by examiner aqueous phase  organic phase

B lymphocytes

Jurkat E6.1 cells

T-lymphocytes

PROCESS AND SUBSTANCES FOR THE RELEASE OF A GROWTH-REGULATING FACTOR FROM ENDOTHELIAL CELLS

CROSS REFERENCE TO RELATED APPLICATIONS

The application is a continuation-in-part of application Ser. No. 09/341,607 filed Oct. 21, 1999, now abandoned, which is a continuation to PCT/AT98/00008 filed Jan. 20, 1998 that claims benefit to Austrian application A73/97 filed Jan. 20, 1997.

It is known that pentacyclic oxindole alkaloids exert pharmacological effects on the immune system. Increased phagocytosis of granulocytes [H. Wagner, Kreutzkamp B., Jurcic K., (1985) *Planta Med.* 51, 419–423] and moderate inhibition of proliferation of leukemic cells [Stuppner H., Sturm S., Geisen G., Zillian U., Konwalinka G. (1993) *Planta Med.* 59, Suppl. A 583] have been demonstrated. A slight but significant lymphocytosis was observed in probands who had taken orally an alkaloid-containing extract of the root of *Uncaria tomentosa* (Willd.) DC. [Keplinger U. (1995) in *Krallendorn: Extract from Radix Uncariae tomentosae* (Willd.) DC., *Information for physicians and pharmacists;* Immodal Pharmaka GmbH, 3rd edn.]. From these findings it was deduced that pentacyclic oxindole alkaloids have immunostimulating or immunomodulating properties. Patents concerning this were granted [U.S. Pat. No. 5,302,611, WO 86100624].

It is known that tetracyclic oxindole alkaloids act on the central nervous system, produce negatively chronotropic and negatively inotropic effects [Kanatani H., Kohda H., Yamasaki K., Hotta I., Nakata Y., Segawa T., Yamanaka E., Aimi N., Sakai S. I. (1984) *J. Pharm. Pharmacol.* 37, 401–404; Zhang W., Liu G. X. (1986) *Act. Pharmacol. Sinica* 7 (5), 426–428; Zhu Y., Guoxiong H. X. (1993) *Chin. J. Pharmacol. Toxicol.* 7 (2), 117–121], block $Ca^{2+}$ transport [Sun A., Liu G., Wang X., Zhang W., Huang X. (1988) *Chin. J. Pharmacol. Toxicol.* 2 (2), 93–97; Zhang W., Liu G., Huang X. (1987) *Act. Pharmacol. Sinica* 8, 425–429], and inhibit the aggregation of blood platelets [Jin R. M., Chen C. X., Li Y. K., Xu P. K. (1991) *Act. Pharmaceut. Sinica* 26 (4), 246–249; Chen C. X., Jin R. M., Li Y. K., Zhong J., Yue L., Chen S. C., Zhou J. Y. (1992) *Act. Pharmacol. Sinica* 13 (2), 126–130].

It is also known that oxindole alkaloids undergo isomerization in solution. Only recently an analysis of the kinetics of the isomerization was reported (Laus G., Brössner D., Senn G., Wurst K. (1996) *J.Chem.Soc., Perkin Trans.* 2, 1931–1936). The production of defined mixtures of isomers is known from U.S. Pat. No. 5,723,625. The alkaloids used in this work were isolated from the roots of *Uncaria tomentosa*. The alkaloid content of a number of these plants was investigated. It was found that two chemotypes of *Uncaria tomentosa* occur in nature. One chemotype of *Uncaria tomentosa* contains mainly the tetracyclic oxindole alkaloids rhynchophylline and isorhynchophylline, the other one contains the pentacyclic oxindole alkaloids pteropodine, isopteropodine, speciophylline, uncarine F, mitraphylline and isomitraphylline. Accordingly, they are designated as tetracyclic alkaloid-type or pentacyclic alkaloid-type [Laus G., Brössner D., Keplinger K. (1997) *Phytochemistry* 45, 855–860]. Transitional forms have also been found in some instances which contain both types of alkaloids in various ratios [Laus G., Keplinger D. (1994) *J. Chromatogr. A* 662, 243–249]. Therefore the tetracyclic as well as the pentacyclic alkaloids were used in the investigations which are described in the following.

General structure of pentacyclic oxindole alkaloids with notation of stereochemistry:

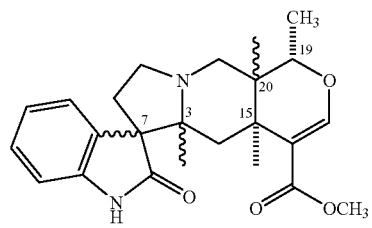

1 Pteropodine 3S, 7R, 15S, 19S, 20S
2 Isopteropodine 3S, 7S, 15S, 19S, 20S
3 Speciophylline 3R, 7S, 15S, 19S, 20S
4 Uncarine F 3R, 7R, 15S, 19S, 20S
5 Mitraphylline 3S, 7R, 15S, 19S, 20R
6 Isomitraphylline 3S, 7S, 15S. 19S, 20R General structure of tetracyclic oxindole alkaloids with notation of stereochemistry:

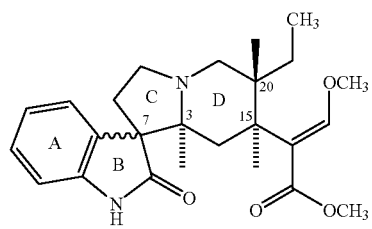

7 Rhynchophylline 3S, 7R, 15S, 20R
8 Isorhynchophylline 3S. 7S, 15S, 20R

DESCRIPTION OF FIGS. 1 TO 4

FIG. 1: Qualitative differentiation of the two chemotypes of *Uncaria tomentosa* by thin-layer-chromatography. Columns 1 and 2 are results from acid and alkaline solutions of *Uncaria tomentosa* containing pentacyclic oxindole alkaloids (IMM-2414), columns 3 and 4 are results from acid and alkaline solutions of *Uncaria tomentosa* containing tetracyclic oxindole alkaloids (IMM-2418), and columns 6 and 7 show results from acid and alkaline mixtures of both. Column 5 is a reference solution.

Figure 2:
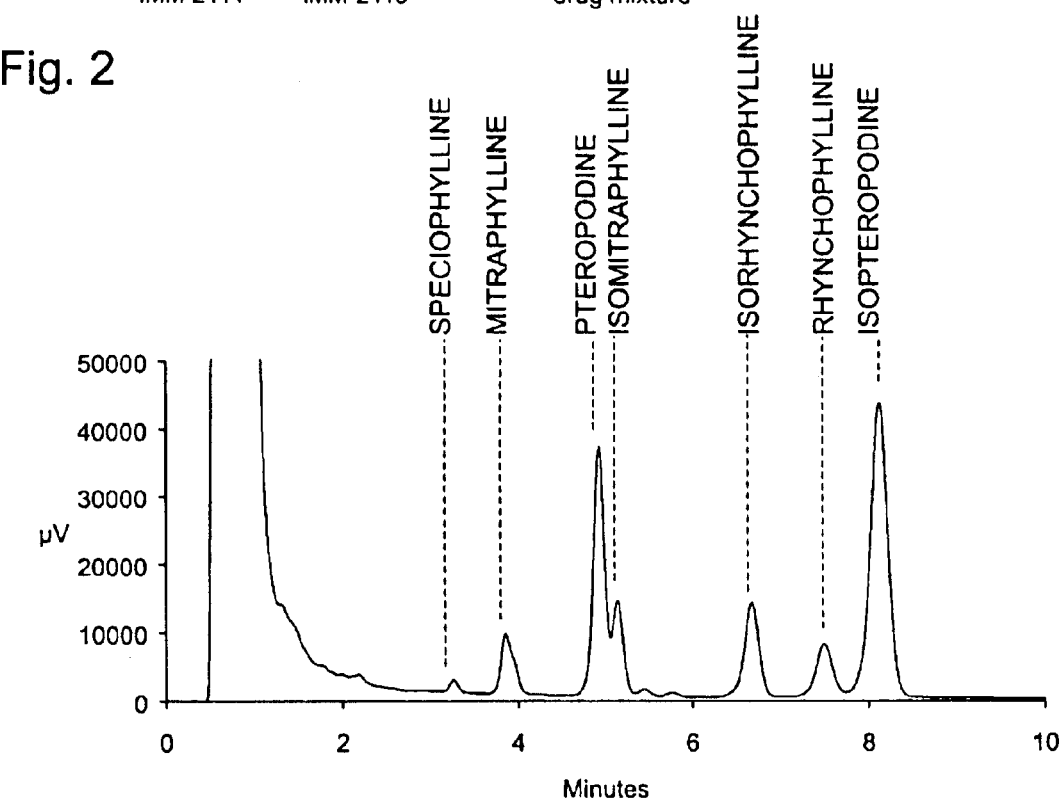

FIG. 2: Separation of pentacyclic and tetracyclic oxindole alkaloids by HPLC.

Figure 3:
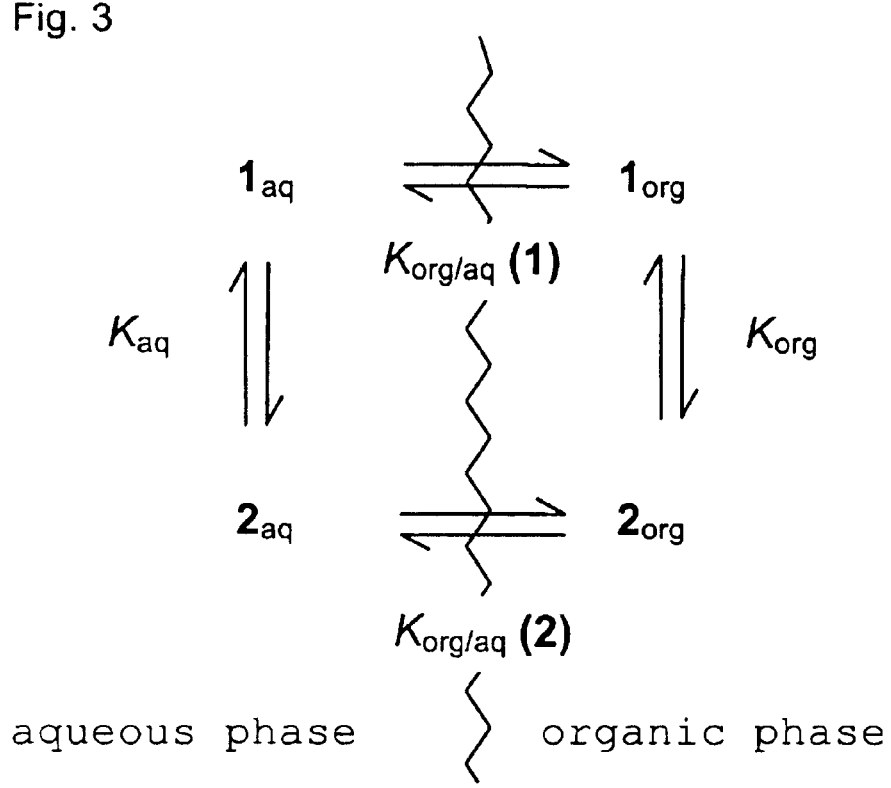

FIG. 3: Equilibria of isomerization $K_{aq}$, $K_{org}$ and partition $K_{org/aq}$ of two isomers (1) and (2) in a two-phase-system, where $$K_{org}(1 \rightarrow 2) = \frac{K_{org/aq}(2)}{K_{org/aq}(1)} K_{aq}(1 \rightarrow 2)$$

Figure 4:
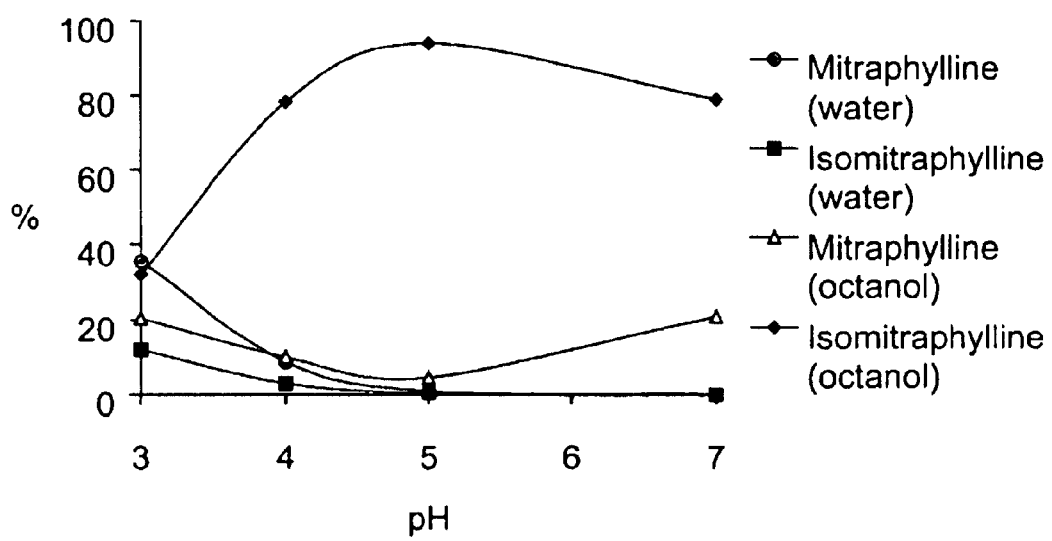

FIG. 4: pH-dependence of equilibrium concentrations (in mol-%) in an octanol-water system containing mitraphylline and isomitraphylline as an example.

Thin-Layer Chromatographic Identification Test

Thin layer chromatography provides an excellent method for the test of identity of the drug, especially when the characteristic pH-dependent isomerization behaviour of the oxindole alkaloids is taken as an additional criterion.

Ajmalicine is proposed as a reference substance because of its similar structure and commercial availability. In order to compensate for variations in chromatographic conditions the $R_f$ values are referred to ajmalicine ($hR_{ajmalicine}$ values, Table 1).

TABLE 1

$hR_{ajmalicine}$ values of the alkaloids

| Alkaloid | $hR_{ajmalicine}$ |
|---|---|
| Speciophylline | 12 |
| Mitraphylline | 26 |
| Uncarine F | 56 |
| Isomitraphylline | 75 |
| Pteropodine | 83 |
| Isopteropodine | 95 |
| Rhynchophylline | 22 |
| Isorhynchophylline | 91 |
| Ajmalicine | 100 |

Test solutions: 1 g of the drug is heated with 50 ml distilled water for 45 minutes at 85° C. The extract is decanted and the drug is washed with 20 ml water. The combined extracts are divided into two portions. One portion is acidified by the addition of 1 drop of hydrochloric acid 7% (approx. pH 4, solutions 1, 3 and 6) and refluxed for 24 h, the second portion is made alkaline with 1 drop of sodium hydroxide solution 8.5% (approx. pH 8, solutions 2, 4 and 7) and maintained at 50° C. for 24 h. Afterwards 2 drops of sodium hydroxide solution 8.5% are added to the acidic solution. All solutions are extracted with 3×5 ml chloroform, collecting at least 4 ml of the organic layer in each extraction step. The extracts are dried by the addition of anhydrous sodium sulfate and the solvent is evaporated. The residues are dissolved in 0.5 ml chloroform and the resulting solutions are used for thin layer chromatography. 1 mg ajmalicine (Fluka, Switzerland) is dissolved in 1 ml chloroform to give the reference solution (solution 5). Spots of 10 μl are applied to TLC-plastic sheets of silica 60 $F_{264}$ (20×20 cm, 0.2 mm thickness of layer; Merck No. 5735). A mixture of ethyl acetate/n-hexane (95:5) is used to develop the chromatogramme, and fluorescence quenching at 254 nm is used for detection.

The possible cases are depicted in FIG. 1. In case of the pentacyclic alkaloid-type *U. tomentosa* spots of six alkaloids are observed. Speciophylline, mitraphylline and pteropodine dominate in solution 1 which was isomerized in acid (column 1), while isopteropodine and isomitraphylline prevail in solution 2 which was isomerized in alkali (column 2). The undesired alkaloids rhynchophylline and isorhynchophylline from tetracyclic alkaloid-type *U. tomentosa* can be seen clearly and exhibit similar dependance on the pH of the isomerized solutions 3 and 4 as mitraphylline and isomitraphylline. Column 5 is the reference compound ajmalicine. Columns 6 and 7 indicate typical drug mixtures. An HPLC chromatogramme which allows the analysis of pentacyclic and tetracyclic oxindole alkaloids is shown in FIG. 2. Method: LiChroCART 125 mm×4 mm (I.D.) columns packed with LiChrospher 100 RP-18 (5 μm) (Merck), thermostatted at 52° C., acetonitrile-aqueous phosphate buffer pH7 (40:60) with a flow of 1.3 ml/min. Detection at 247 nm.

Composition of Alkaloid Mixtures Used

As oxindole alkaloids undergo isomerization in aqueous solution, no single isomers but groups of isomers were employed. First, a mixture of pentacyclic alkaloids (IMM-2414) was used, then the isomer groups of mitraphylline (IMM-2417), rhynchophylline (IMM-2418) and pteropodine (IMM-2435) were used. The composition of the mixtures is given in Table 2. The composition of the alkaloid mixtures was determined by HPLC analyses.

TABLE 2

Composition of alkaloid mixtures used

| Alkaloid | Code IMM-2414 | IMM-2417 | IMM-2418 | IMM-2435 |
|---|---|---|---|---|
| Speciophylline | 4% | — | — | 4% |
| Uncarine F | 6% | — | — | 6% |
| Pteropodine | 28% | — | — | 30% |
| Isopteropodine | 57% | — | — | 60% |
| Mitraphylline | 2% | 33% | — | — |
| Isomitraphylline | 3% | 67% | — | — |
| Rhynchophylline | — | — | 40% | — |
| Isorhynchophylline | — | — | 60% | — |

Comments:
The percent quotations are percents by weight.
The composition of the alkaloid mixtures was determined by HPLC analysis.

Simple derivatives were also used: the alkaloid carboxylic acids (IMM-2413) prepared by alkaline hydrolysis of the alkaloid mixture (IMM-2414), and the alkaloid N-oxides (IMM-2433) prepared by oxidation of the mixture (IMM-2414) using hydrogen peroxide.

Distribution of the Alkaloids in Biological Systems

Cells in a culture medium can be viewed as a two-phase system consisting of water and lipids. The distribution of the alkaloids in cell cultures and in mixtures of octanol and water was studied. It was found that the various isomers behave differently (Table 3). The alkaloids were partitioned between equal volumes of octanol and aqueous phosphate buffer pH 7 (0.01 M) at 20° C. The concentrations c of the alkaloids were determined by HPLC analysis and the coefficients of distribution $$K_{O/W} = \frac{c_{(in\ octanol)}}{c_{(in\ water)}}$$

were calculated.

TABLE 3

Common logarithm of the partition coefficients $K_{O/W}$ at pH 7

| Alkaloid | log $K_{O/W}$ |
|---|---|
| Pteropodine | 2.9 |
| Isopteropodine | 3.2 |
| Speciophylline | 1.4 |
| Uncarine F | 3.1 |
| Mitraphylline | 2.5 |
| Isomitraphylline | 2.8 |
| Rhynchophylline | 2.7 |
| Isorhynchophylline | 3.1 |

As expected the equilibrium of isomers in a two-phase system ($1_{aq} \leftrightarrow 1_{org}$, $2_{aq} \leftrightarrow 2_{org}$, FIG. 3) depends not only on the pH value of the aqueous phase but also on the amount and nature of the organic phase, For an example, the equilibria of mitraphylline and isomitraphylline in an octanol-water system (1:1) at pH values from 3 to 7 are shown (FIG. 4). It can be seen that in the pH range from 4 to 7 isomitraphylline is predominant in the octanol phase, with a maximum of 94 mol-% at approximately pH 5. However, below pH 3 mitraphylline begins to prevail in the aqueous phase. At no pH value is isomitraphylline produced in the aqueous phase to a reasonable extent. Therefore, the distribution of the isomers in a 2-phase system is clearly different compared to the situation in a purely aqueous solution.

In EA.hy926 endothelial cell cultures which were incubated with various alkaloid mixtures (c≈1 µM) a decline of the concentrations of isopteropodine or isomitraphylline, respectively, was observed after 7 days, whereas in contrast the concentration of isorhynchophylline remained nearly constant (Table 4). A RPMI-1640 culture medium (Sigma-Aldrich Company, St. Louis, USA) completed with 10% by volume fetal calf serum, 2 mM glutamin, 50 units/ml penicillin G, and 50 µg/ml streptomycin was used.

TABLE 4

Change of the alkaloid concentrations (mg/l) in the RPMI-1640 nutrient medium of EA.hy926 endothelial cell cultures after 7 days

| Stimulant (concentration) | Alkatoid | Start | 7 Days |
|---|---|---|---|
| IMM-2414 (1.0 µM) | Isopteropodine | 0.22 | 0.12 |
| | Pteropodine | 0.10 | 0.16 |
| | Total | 0.32 | 0.28 |
| IMM-2417 (1.0 µM) | Isomitraphylline | 0.28 | 0.14 |
| | Mitraphylline | 0.10 | 0.11 |
| | Total | 0.38 | 0.25 |
| IMM-2418 (1.1 µM) | Isorhynchophylline | 0.27 | 0.27 |
| | Rhynchophylline | 0.15 | 0.13 |
| | Total | 0.42 | 0.40 |
| IMM-2435 (1.4 µM) | Isopteropodine | 0.35 | 0.18 |
| | Pteropodine | 0.11 | 0.20 |
| | Total | 0.46 | 0.38 |

Comments:
IMM-2414 = solution of standard mixture of pentacyclic alkaloids in medium
IMM-2417 = solution of mixture of isomers of mitraphylline in medium
IMM-2418 = solution of mixture of isomers of rhynchophylline in medium
IMM-2435 = solution of mixture of isomers of pteropodine in medium The solubility of the alkaloids in cell membranes does not offer an explanation for the different changes of concentration. Rather, the decline in concentration is a consequence of physiological processes in the cytosol. Compared with pure medium, the isomerization takes a different course in the presence of endothelial cells. Within the 7 days of an experiment (EA.hy926 endothelial cells in RPMI-1640: pH 7.5 at the start, pH 8.1 after 7 days) an untypical mixture of isomers is formed which contains pteropodine and isopteropodine or mitraphylline and isomitraphylline, respectively, in a ratio of approx. 1:1, whereas in contrast rhynchophylline and isorhynchophylline isomerize to give a typical equilibrium mixture in a ratio of 1:2. Of course, activity of single isomers cannot be evaluated in this test model because of the isomerization. But it can be established that a turnover takes place in the case of the pentacyclic but not tetracyclic alkaloids.

SUMMARY OF THE INVENTION

A substance for release from endothelial cells a factor that increases the proliferation of lymphocytes and decreases the proliferation of lymphoblasts, leukemic and virus-transformed cells, said substance comprising pentacyclic oxindole alkaloids. The aforementioned substance can be produced from plant material of *Uncaria tomentosa* (Willd.) DC. The substance may optionally comprise both pentacyclic and tetracyclic oxindoles, at least 50% being of the pentacyclic alkaloid type.

Experiments in Cell Cultures

The effect of the alkaloids was studied in endothelial cells because they are known for interactions with immunologic reactions [Kirchner H., Kruse A., Neustock P., Rink L. (1993) *Cytokine und Interferone: Botenstoffe des Immunsystems*, 61]. It was recognized that the pentacyclic alkaloids (c≈1 µM) induced transformed EA.hy926 endothelial cells [Edgell C.-J. S., McDonald C. C., Graham J. B. (1983) *Proc. Nat. Acad. Sci. USA* 80, 3734–3737) as well as normal human umbilical vein endothelial cells (HUVEC, ATCC CRL-1730) to release a factor into the culture medium which significantly affects the proliferation of lymphocytes. In general, RPMI-1640 was used as the culture medium for EA.hy926 endothelial cells and lymphocytes, completed with 10% fetal calf serum, 2 mM glutamin, 50 units/ml penicillin G and 50 µg/ml streptomycin. For human umbilical vein endothelial cells HAM F12 (Sigma-Aldrich Company, St. Louis, USA) was used as the culture medium, completed with 10% fetal calf serum, 60 µg/ml Endothelial Cell Growth Supplement and 100 µg/ml heparin.

DESCRIPTION OF FIGS. 5 TO 10

Figure 5:
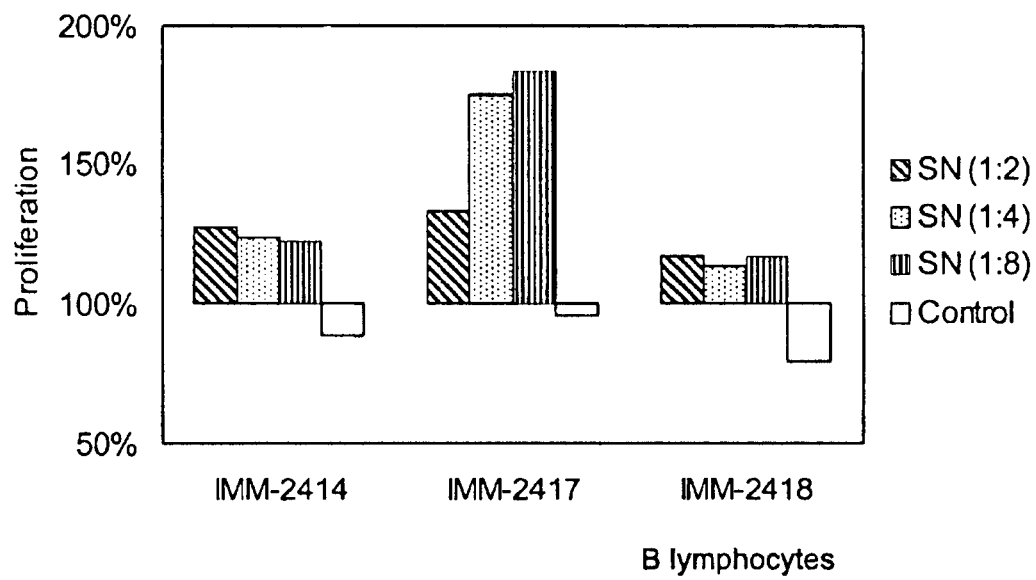

FIG. 5: Increase of proliferation of normal human B lymphocytes, stimulated by supernatants of EA.hy926 cells which were grown in the presence of 1 µM IMM-2414, IMM-2417, IMM-2418.

Figure 6:
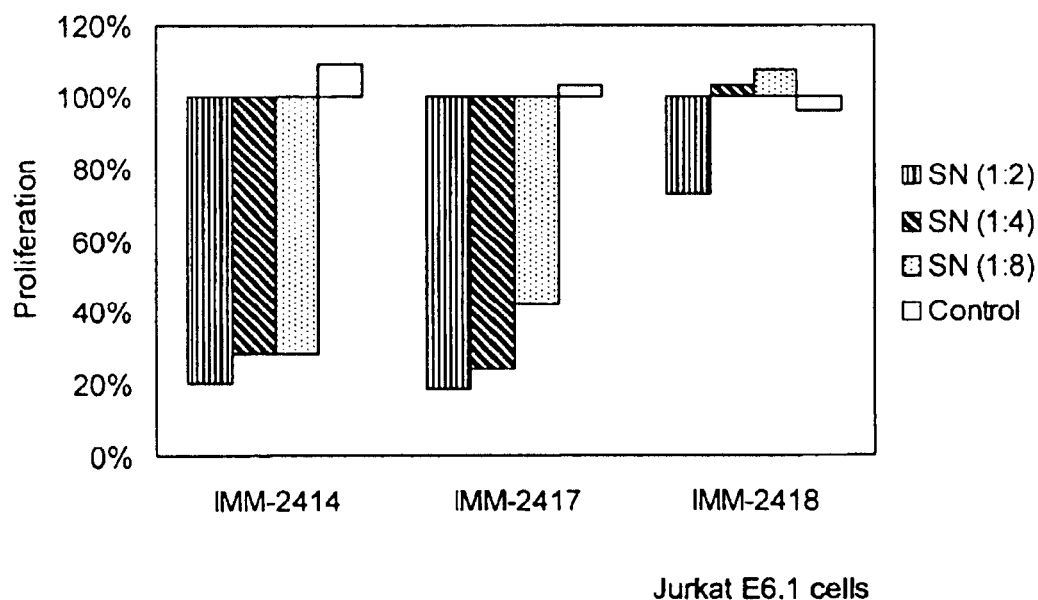

FIG. 6: Inhibition of the proliferation of Jurkat cells (ATCC E6.1), treated with supernatants of EA.hy926 cells which were grown in the presence of 1 µM IMM-2414, IMM-2417, IMM-2418.

Figure 7:
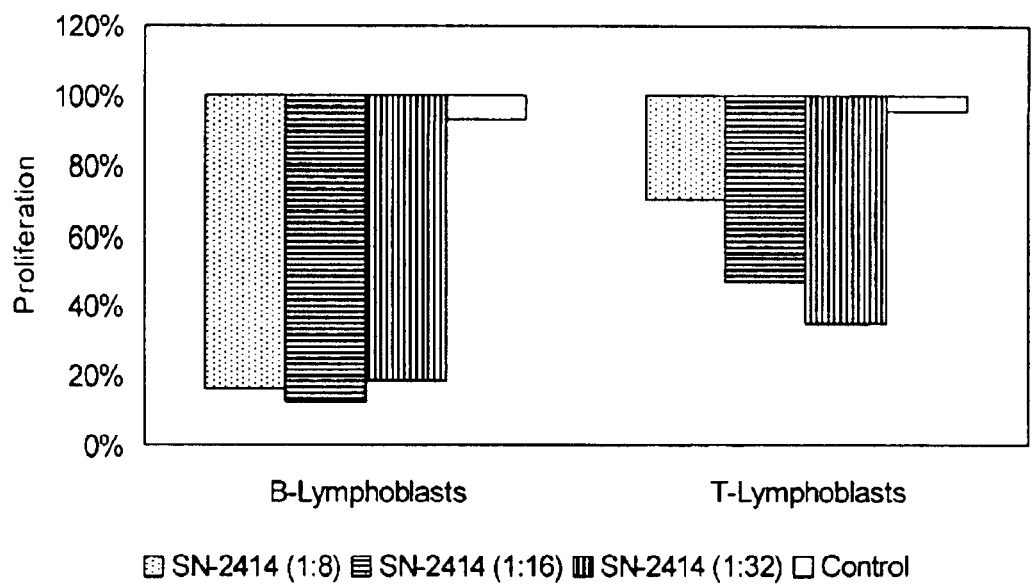

FIG. 7: Inhibition of the proliferation of highly activated human B and T lymphocytes (lymphoblasts) treated with supernatants of EA.hy926 cells (SN) which were grown in the presence of 1 µM IMM-2414.

Figure 8:
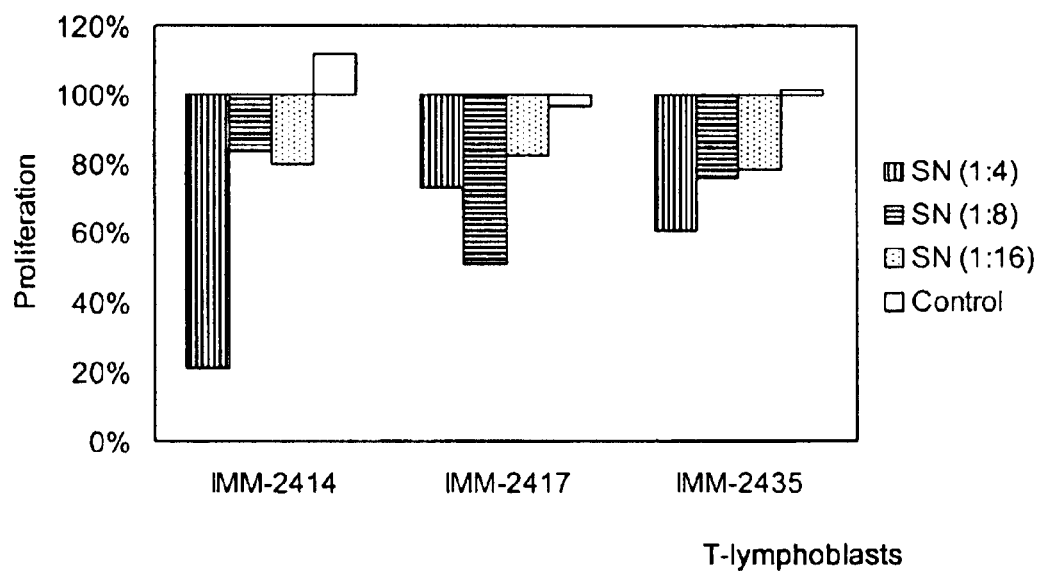

FIG. 8: Inhibition of the proliferation of highly activated human T lymphocytes (lymphoblasts) treated with the alkaloids IMM-2414, IMM-2417, IMM-2435 or with supernatants of EA.hy926 cells (SN) which were grown in the presence of 1 µM IMM-2414, IMM-2417, IMM-2435.

Figure 9:
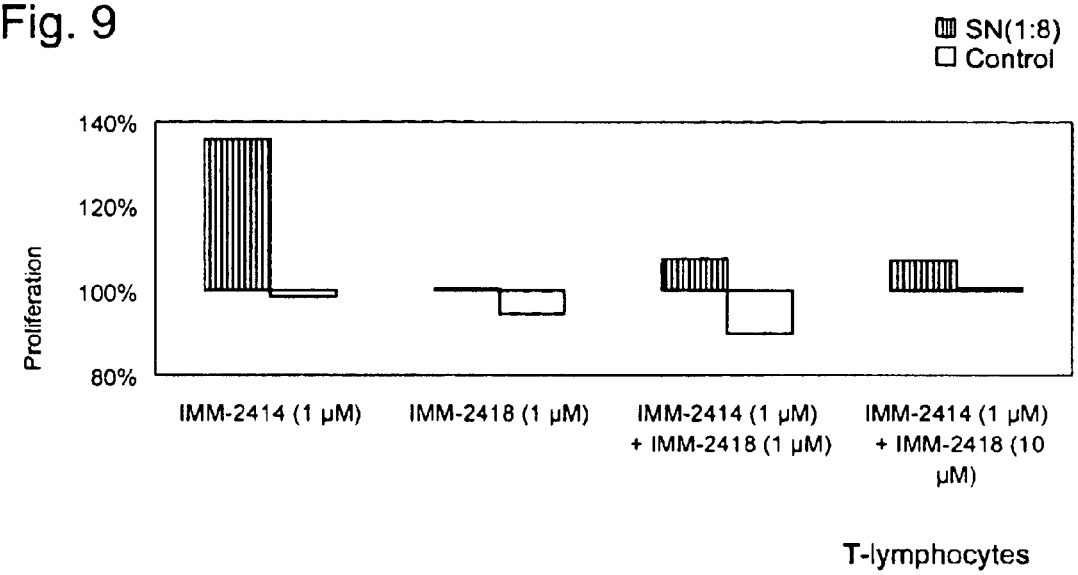

FIG. 9: Proliferation of normal human T lymphocytes, treated with IMM-2414 and/or IMM-2418, or with supernatants of EA.hy926 cells (SN) which were grown in the presence of 1 µM IMM-2414 and/or IMM-2418.

Figure 10:
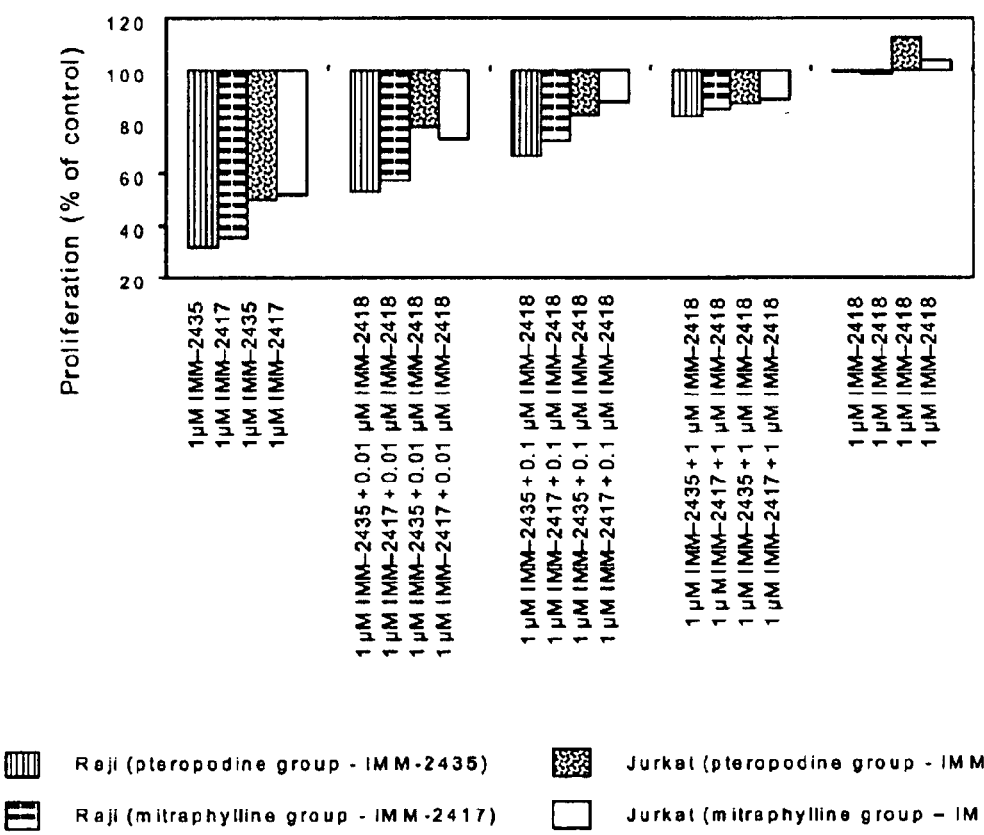

FIG. 10: Antagonistic effect of tetracyclic oxindole alkaloids (TOA) on the biological activity on Raji and Jurkat cells caused by pentacyclic oxindole alkaloids (POA).

The effects of this factor on lymphocytes were investigated in detail. It was found that immortalized cells, e.g. the Epstein-Barr virus-transformed lymphoblastoid cell line Raji or the leukaemic cell line Jurkat, and normal human B and T lymphocytes (isolated from whole blood of normal donors) are affected by the factor in different ways:

1. Supernatants (SN) of endothelial cell cultures stimulated with IMM-2414 for 7 days were added to normal human non-activated or weakly activated B and T lymphocyte cultures in several concentrations. An increased proliferation of the lymphocytes was measured by [$^3$H]thymidine uptake after 5 days (Table 5). Thus, the lymphocytes were treated with 1 µCi [$^3$H] thymidine for 18 hours, harvested on nitrocellulose, and radioactivity was measured in a scintillation counter (cpm=counts per minute). Every assay was performed in triplicate.

TABLE 5

Proliferation (cpm after [$^3$H]thymidine uptake) of normal human non-activated or weakly activated B and T lymphocytes in medium RPMI-1640

| Stimulant (dilution) | B lymphocytes | T lymphocytes |
|---|---|---|
| Medium | 363 ± 213 | 349 ± 114 |
| IMM-2414 (1 µM) | 352 ± 323 | 332 ± 82 |
| and stimulated with EA.hy926 endothelial cell culture supernatants | | |
| SN-Medium (1:4) | 1015 ± 618 | 591 ± 252 |
| SN-2414 (1:4) | 1527 ± 540 | 1242 ± 752*** |
| SN-Medium (1:8) | 1381 ± 390 | 493 ± 278 |
| SN-2414 (1:8) | 2039 ± 530*** | 1084 ± 549**** |
| SN-Medium (1:16) | 1263 ± 299 | 371 ± 151 |
| SN-2414 (1:16) | 1795 ± 584* | 549 ± 250** |

Comments:
Medium = RPMI-1640 completed as specified above
IMM-2414 = solution of standard mixture of pentacyclic alkaloids in medium
SN-Medium = supernatant of endothelial cell culture in medium, diluted with medium in the ratio given
SN-2414 = supernatant of endothelial cell culture stimulated with the standard mixture of pentacyclic alkaloids in medium for 7 days, diluted with medium in the ratio given
Mean values ± standard deviation of at least 7 experiments are given. Significance was evaluated with Student's t-test for paired samples:
*P < 0.05, P < 0.01, *P < 0.005, ****P < 0.001.

It can be seen that the alkaloids alone do not have an effect compared to the blank medium. The supernatants of non-stimulated endothelial cell cultures (SN-Medium) increase the proliferation, and the supernatants of cells stimulated with IMM-2414 increase the proliferation even more. The maximum effect was obtained with T lymphocytes at a dilution of 1:8 and with B lymphocytes at 1:4 of the supernatant SN-2414.

2. Supernatants of endothelial cell cultures (SN-2414) stimulated with IMM-2414 for 7 days and non-stimulated endothelial cell cultures (SN-medium) were added to transformed cells (Raji ATCC CCL86 and Jurkat ATCC E6.1) in several concentrations. In contrast to the B and T lymphocytes, an inhibition of proliferation of the transformed cells was measured by [$^3$H]thymidine uptake after 2 days (Table 6). Cultures of the myeloid cell line U937 (ATCC CRL1593.2) were also studied. The transformed cells were treated with 0.5 µCi VH]thymidine for 5 hours, harvested on nitrocellulose, and radioactivity was measured in a scintillation counter (cpm=counts per minute).

TABLE 6

Proliferation (cpm after [$^3$H]thymidine uptake) of various cell lines in medium RPMI-1640

| Stimulant (dilution) | Raji CCL86[a] | Jurkat E6.1[a] | U937 CRL1593.2[b] |
|---|---|---|---|
| Medium | 21621 ± 5755 | 35085 ± 13876 | 121349 ± 18653 |
| IMM-2414 (1 µM) | 21698 ± 6299 | 35688 ± 14020 | 123346 ± 26412 |
| and under the influence of EA.hy926 endothelial cell culture supernatants | | | |
| SN-Medium (1:2) | 32967 ± 9652 | 26544 ± 17492 | 86115 ± 30792 |
| SN-2414 (1:2) | 4801 ± 3766*** | 4282 ± 3186** | 84736 ± 33654 |
| SN-Medium (1:4) | 30919 ± 11134 | 34716 ± 17394 | 101093 ± 24813 |
| SN-2414 (1:4) | 9178 ± 7671 | 7163 ± 6268*** | 94257 ± 30331 |
| SN-Medium (1:8) | 21976 ± 7443 | 41428 ± 16648 | 118634 ± 19980 |
| SN-2414 (1:8) | 11357 ± 5308 | 8044 ± 3921*** | 107771 ± 30975 |

Comments:
Medium = RPMI-1640 completed as specified above
IMM-2414 = solution of standard mixture of pentacyclic alkaloids in medium
SN-Medium = supernatant of endothelial cell culture in medium, diluted with medium in the ratio given
SN-2414 = supernatant of endothelial cell culture stimulated with the standard mixture of pentacyclic alkaloids in medium for 7 days, diluted with medium in the ratio given
Mean values ± standard deviation of at least [a]7 experiments, [b]3 experiments are given.
Significance was evaluated with Student's t-test for paired samples:
*P < 0.05, P < 0.01, *P < 0.005, ****P < 0.001.

It can be seen that the alkaloids alone do not have an effect compared to the blank medium. The supernatants of the IMM-2414-stimulated endothelial cell cultures inhibit the profileration of Raji and Jurkat cells dose-dependently, whereas the myeloid cell line U937 is not affected.

3. The anti-proliferative effect on Raji and Jurkat cells is not due to cytotoxicity, as shown by unchanged viability of the cells (Table 7).

TABLE 7

Viability (in %) of Raji and Jurkat cells after stimulation with IMM-2414 or supernatants at EA.hy926 endothelial cell cultures which were cultivated with IMM-2414

| Stimulant (dilution) | Raji CCL86 | | Jurkat E6.1 | |
|---|---|---|---|---|
| | 1st day | 2nd day | 1st day | 2nd day |
| Medium | 93.5 | 95.1 | 95.8 | 93.7 |
| IMM-2414 (1 µM) | 96.8 | 90.1 | 95.2 | 95.8 |
| and under the influence of EA.hy926 endothelial cell culture supernatants | | | | |
| SN-Medium (1:2) | 95.4 | 95.3 | 96.4 | 92.0 |
| SN-2414 (1:2) | 98.4 | 92.2 | 94.4 | 92.2 |

Comments:
Medium = RPMI-1640 completed as specified above
IMM-2414 = solution of standard mixture of pentacyclic alkaloids in medium
SN-Medium = supernatant of endothetial cell culture in medium, diluted with medium in the ratio given
SN-2414 = supernatant of endothelial cell culture stimulated with the standard mixture of pentacyclic alkaloids in medium for 7 days, diluted with medium in the ratio given The viability of the cells was determined by trypan blue exclusion after 1 and 2 days of stimulation with IMM-2414. In all cases the viability was higher than 90%.

4. Supernatants of endothelial cell cultures stimulated with IMM-2414, IMM-2417 or IMM-2435 for 7 days (SN-2414, SN-2417, SN-2435) and non-stimulated (SN-medium) were added to cultures of human highly activated T lymphocytes (lymphoblasts) in several concentrations (Table 8).

TABLE 8

Proliferation (cpm after [³H]thymidine uptake) of human highly activated T lymphocytes (lymphoblasts) in medium RPMI-1640

| Stimulant (dilution) | T lymphoblasts |
|---|---|
| Medium | 4065 |
| IMM-2414 | 4557 |
| IMM-2417 | 3929 |
| IMM-2435 | 4124 |
| and under the influence of EA.hy926 endothelial cell supernatants | |
| SN-medium (1:4) | 3113 |
| SN-2414 (1:4) | 652 |
| SN-2417 (1:4) | 2285 |
| SN-2435 (1:4) | 1887 |
| SN-medium (1:8) | 3139 |
| SN-2414 (1:8) | 2628 |
| SN-2417 (1:8) | 1595 |
| SN-2435 (1:8) | 2380 |
| SN-medium (1:16) | 2320 |
| SN-2414 (1:16) | 1852 |
| SN-2417 (1:16) | 1913 |
| SN-2435 (1:16) | 1821 |

Comments:
Medium = RPMI-1640 completed as specified above
IMM-2414 = solution of standard mixture of pentacyclic alkaloids in medium
IMM-2417 = solution of mixture of isomers of mitraphylline in medium
IMM-2435 = solution of mixture of isomers of pteropodine in medium
SN-medium = supernatant of endothelial cell culture in medium, diluted with medium in the ratio given
SN-2414 = supernatant of endothelial cell culture stimulated with the standard mixture of pentacyclic alkaloids in medium for 7 days, diluted with medium in the ratio given
SN-2417 = supernatant of endothelial cell culture stimulated with the mixture of isomers of mitraphylline in medium for 7 days, diluted with medium in the ratio given
SN-2435 = supernatant of endothelial cell culture stimulated with the mixture of isomers of pteropodine in medium for 7 days, diluted with medium in the ratio given.
All values result from single experiments.

It can be seen that the alkaloids alone do not have an effect compared to the blank medium. The supernatants of the non-stimulated endothelial cell cultures (SN-medium) already inhibit the proliferation, the supernatants (SN-2414, SN-2417, SN-2435) of endothelial cell cultures stimulated with IMM-2414, IMM-2417, IMM-2435 further enhance this effect (FIG. 8). The dose dependance of the effect is clearly seen.

5. Supernatants of endothelial cell cultures (SN-2412) stimulated with IMM-2414 for 7 days and non-stimulated (SN-medium) were added to highly activated B or T lymphocyte cultures (lymphoblasts from peripheral blood or tonsils) in several concentrations. Table 9 shows an inhibition of proliferation of the lymphocytes, measured by [³H]thymidine uptake (cpm=counts per minute).

TABLE 9

Inhibition of the proliferation (cpm after [³H]thymidine uptake) of highly activated human B and T lymphocytes (lymphoblasts) in medium RPMI-1640

| Stimulant (dilution) | B lymphoblasts | T lymphoblasts |
|---|---|---|
| Medium | 17840 | 2186 |
| IMM-2414 (1 µM) | 16610 | 2097 |
| and under the influence of EA.hy926 endothelial cell culture supernatants | | |
| SN-Medium (1:8) | 9594 | 1254 |
| SN-2414 (1:8) | 1527 | 684 |

TABLE 9-continued

Inhibition of the proliferation (cpm after [³H]thymidine uptake) of highly activated human B and T lymphocytes (lymphoblasts) in medium RPMI-1640

| Stimulant (dilution) | B lymphoblasts | T lymphoblasts |
|---|---|---|
| SN-Medium (1:16) | 13865 | 1554 |
| SN-2414 (1:16) | 1699 | 728 |
| SN-Medium (1:32) | 13903 | 2049 |
| SN-2414 (1:32) | 2534 | 720 |

Comments:
Medium = RPMI-1640 completed as specified above
IMM-2414 = solution of standard mixture of pentacyclic alkaloids in medium
SN-Medium = supernatant of endothelial cell culture in medium, diluted with medium in the ratio given
SN-2414 = supernatant of endothelial cell culture stimulated with the standard mixture of pentacyclic alkaloids in medium for 7 days, diluted with medium in the ratio given
All values result from single experiments.

It can be seen that the alkaloids alone do not have an effect compared to the blank medium. The supernatants of the non-stimulated endothelial cell cultures (SN-Medium) already inhibit the proliferation, the supernatants of the IMM-2414-stimulated endothelial cell cultures (SN-2414) further enhance this effect (FIG. 7). The dose dependence of the effect is clearly seen.

6. In another experiment, supernatants of HUVEC endothelial cell cultures stimulated with IMM-2414 for 7 days (SN-2414) and non-stimulated (SN-medium) were added to T lymphocyte cultures in several concentrations. The influence on proliferation of the lymphocytes was measured by [²H]thymidine uptake (cpm=counts per minute). The results are shown in Table 10.

TABLE 10

Proliferation (cpm after [³H]thymidine uptake) of human normal T lymphocytes in medium HAM F12

| Stimulant (dilution) | T lymphocytes |
|---|---|
| Medium | 864 |
| IMM-2414 (2 µM) | 885 |
| and under the influence of supernatants from HUVEC endothelial cell cultures | |
| SN-Medium (1:4) | 1339 |
| SN-2414 (1:4) | 1887 |
| SN-Medium (1:8) | 1106 |
| SN-2414 (1:8) | 1509 |
| SN-Medium (1:16) | 913 |
| SN-2414 (1:16) | 1279 |

Comments:
Medium = HAM F12 completed as specified above
IMM-2414 = solution of standard mixture of pentacyclic alkaloids in medium
SN-Medium = supernatant of endothelial cell culture in medium, diluted with medium in the ratio given
SN-2414 = supernatant of endothelial cell culture stimulated with the standard mixture of pentacyclic alkaloids in medium for 7 days, diluted with medium in the ratio given
All values result from single experiments.

It can be seen that the alkaloids alone do not have an effect compared to the blank medium. The supernatants of the non-stimulated endothelial cell cultures (SN-medium) already increase the proliferation, the supernatants of the IMM-2414-stimulated endothelial cell cultures (SN-2414) further enhance this effect. The dose dependance of the effect is clearly seen. Thus, activities produced by HUVEC culture supernatants are somewhat weaker but significant, too.

7. The release of the growth-factor was effected by the groups of isomers of the pentacyclic alkaloids pteropodine or mitraphylline (IMM-2414, IMM-2417 or IMM-2435), but not by the group of isomers of the tetracyclic alkaloid rhynchophylline (IMM-2418), as can be seen in Table 11. Supernatants of endothelial cell cultures stimulated with IMM-2414, IMM-2417 or IMM-2418 for 7 days (SN-2414, SN-2417, SN-2418) and non-stimulated (SN-medium) were added to cell cultures in several concentrations. The influence on proliferation of the cells was measured by [$^3$H]thymidine uptake (cpm=counts per minute).

TABLE 11

Proliferation (cpm after [$^3$H] thymidine uptake) of Jurkat cells (ATCC E6.1) and normal human B lymphocytes in medium RPMI-1640

| Stimulant (dilution) | Jurkat E6.1[a] | Stimulant (dilution) | B lymphocytes[b] |
|---|---|---|---|
| Medium | 32737 | Medium | 632 |
| IMM-2414 (1 µM) | 35688 | IMM-2414 (1 uM) | 560 |
| IMM-2417 (1 µM) | 33700 | IMM-2417 (1 µM) | 606 |
| IMM-2418 (1 µM) | 31440 | IMM-2418 (1 µM) | 501 |
| and stimulated with supernatants of EA.hy928 cells | | | |
| SN-Medium (1:2) | 21673 | SN-Medium (1:8) | 1639 |
| SN-2414 (1:2) | 4282 | SN-2414 (1:8) | 2082 |
| SN-2417 (1:2) | 3953 | SN-2417 (1:8) | 2183 |
| SN-2418 (1:2) | 15724 | SN-2418 (1:8) | 1908 |
| SN-Medium (1:4) | 25288 | SN-Medium (1:16) | 1306 |
| SN-2414 (1:4) | 7163 | SN-2414 (1:16) | 1617 |
| SN-2417 (1:4) | 6068 | SN-2417 (1:16) | 2289 |
| SN-2418 (1:4) | 26132 | SN-2418 (1:16) | 1474 |
| SN-Medium (1:8) | 28124 | SN-Medium (1:32) | 1231 |
| SN-2414 (1:8) | 8044 | SN-2414 (1:32) | 1605 |
| SN-2417 (1:8) | 11783 | SN-2417 (1:32) | 2258 |
| SN-2418 (1:8) | 30190 | SN-2418 (1:32) | 1437 |

Comments:
Medium = RPMI-1640 completed as specified above
IMM-2414 = solution of standard mixture of pentacyclic alkaloids in medium
IMM-2417 = solution of mixture of isomers of mitraphylline in medium
IMM-2418 = solution of mixture of isomers of rhynchophylline in medium
SN-medium = supernatant of endothelial cell culture in medium, diluted with medium in the ratio given
SN-2414 = supernatant of endothelial cell culture stimulated with the standard mixture of pentacyclic alkaloids in medium for 7 days. diluted with medium in the ratio given
SN-2417 = supernatant of endothelial cell culture stimulated with the mixture of isomers of mitraphylline in medium for 7 days, diluted with medium in the ratio given
SN-2418 = supernatant of endothelial cell culture stimulated with the mixture of isomers of rhynchophylline in medium for 7 days, diluted with medium in the ratio given
[a]Mean values of at least 3 parallel experiments.
[b]Results of single experiments.

The alkaloids alone do not have an effect compared to the blank medium. The supernatants of the non-stimulated endothelial cell cultures (SN-medium) already inhibit the proliferation of the Jurkat cells (FIG. 6) and increase the proliferation of the B lymphocytes (FIG. 5). The supernatants of the IMM-2414 and IMM-2417-stimulated endothelial cell cultures (SN-2414, SN-2417) further enhance this effect. The dose dependance of these effects are clearly seen. It is to notice that supernatants of endothelial cell cultures stimulated with IMM-2417 increase the proliferation of B lymphocytes even when diluted in the ratio 1:16 or 1:32, whereas the activity of endothelial cell cultures stimulated with IMM-2414 already decreases (SN-2414). The supernatants of the IMM-2418-stimulated endothelial cell cultures (SN-2418) produce no effect compared to supernatants of non-stimulated endothelial cell cultures (SN-medium).

8. Rather it was shown that the tetracyclic alkaloids act antagonistically on the production and/or release of the growth-factor. This could be connected with their known capability of blocking $Ca^{2+}$ transport. Furthermore, they reduce the influence of the factor on the proliferation of T-lymphocytes in a dose-dependent manner (addition of 1 µM IMM-2418 to an active supernatant reduces the activity by 10%, 10 µM by 20%). Results are shown in Table 12. Supernatants of endothelial cell cultures stimulated with IMM-2414 and/or IMM-2418 for 7 days (SN-2414, SN-2418, SN-2414/2418 and SN-2414/10×2418) and non-stimulated (SN-medium) were added to T lymphocyte cultures in several concentrations. The influence on proliferation of the lymphocytes was measured by [$^3$]thymidine uptake (cpm=counts per minute).

TABLE 12

Proliferation (cpm after [$^3$H]thymidine uptake) of human normal T lymphocytes in medium RPMI-1640

| Stimulant (dilution) | T lymphocytes |
|---|---|
| Medium | 598 ± 429 |
| IMM-2414 (1 µM) | 590 ± 420 |
| IMM-2418 (1 µM) | 564 ± 409 |
| IMM-2414 (1 µM)/2418 (1 µM) | 536 ± 416 |
| IMM-2414 (1 µM)/2418 (10 µM) | 602 ± 504 |
| and under the influence of EA.hy926 endothelial cell supernatants | |
| SN-Medium (1:4) | 1900 ± 1603 |
| SN-2414 (1:4) | 2694 ± 1662 |
| SN-2418 (1:4) | 1956 ± 1618 |
| SN-2414/2418 (1:4) | 1890 ± 1712 |
| SN-2414/10 × 241B (1:4) | 1479 ± 1191 |
| SN-Medium (1:8) | 1581 ± 1448 |
| SN-2414 (1:8) | 2144 ± 1402 |
| SN-2418 (1:8) | 1588 ± 1393 |
| SN-2414/2418 (1:8) | 1698 ± 1644 |
| SN-2414/10 × 2418 (1:8) | 1692 ± 1422 |

Comments:
Medium = RPMI-1640 completed as specified above
IMM-2414 = solution of standard mixture of pentacyclic alkaloids in medium
IMM-2418 = solution of mixture of isomers of rhynchophylline in medium
SN-medium = supernatant of endothelial cell culture in medium, diluted with medium in the ratio given
SN-2414 = supernatant of endothelial cell culture stimulated with the standard mixture of pentacyclic alkaloids in medium for 7 days. diluted with medium in the ratio given
SN-2418 = supernatant of endothelial cell culture stimulated with the mixture of isomers of rhynohophylline in medium for 7 days, diluted with medium in the ratio given
SN-2414/2418 = supernatant of endothelial cell culture stimulated with the standard mixture of pentacyclic alkaloids and the mixture of isomers of rhynchophilline in equal parts in medium for 7 days, diluted with medium in the ratio given
SN-2414/10 × 2418 = supernatant of endothelial cell culture stimulated with the standard mixture of pentacyolic alkaloids and the mixture of isomers of rhynchophilline (1:10) in medium for 7 days, diluted with medium in the ratio given. The values represent mean values ± standard deviation of 7 experiments.

It can be seen that the alkaloids alone do not have an effect compared to the blank medium. The supernatants of the non-stimulated endothelial cell cultures (SN-medium) already increase the proliferation, the supernatants of the IMM-2414-stimulated endothelial cell cultures (SN-2414) further enhance this effect. The supernatants of the IMM-2418 stimulated endothelial cell cultures (SN-2418) do not have an effect compared to the supernatants of non-stimulated endothelial cell cultures (SN-medium). The supernatants of the IMM-2414 and IMM-2418-stimulated endothelial cell cultures (SN-2414/2418) do not have an effect, either, compared to the supernatants of non-stimulated endothelial cell cultures (SN-medium). IMM- 2418 therefore cancels the effect of IMM-2414 (FIG. 9). Highly concentrated (diluted 1:4) supernatants of endothelial cell cultures stimulated with tenfold concentrated IMM-2418 (SN-2414/10×2418) produce of slight inhibition of proliferation compared to supernatants of non-stimulated cultures (SN-medium)

9. Admixture of 0.01, 0.1 and 1 µM tetracyclic oxindole alkaloids to 1 µM pentacyclic oxindole alkaloids (pteropodine isomers as well as mitraphylline isomers) as stimulant reduced the effect of the supernatants on Raji and Jurkat cells in a dose-dependent manner. Supernatants (SN) of endothelial cell cultures stimulated with IMM-2417, IMM-2435 and/or IMM-2418 for 7 days and non-stimulated (SN-medium=control) were added to transformed lymphoblastoid Raji and Jurkat cell cultures. The inhibition of proliferation of the cells was measured by [$^3$H]thymidine uptake (cpm= counts per minute). The tetracyclic oxindole alkaloids act antagonistically on the pentacyclic oxindole alkaloids in a dose-dependent manner (FIG. 10). This could be connected with their known capability of blocking $Ca^{2+}$ transport. Furthermore, they reduce the influence of the factor on the proliferation of T-lymphocytes in a dose-dependent manner (addition of 1 µM IMM-2418 to an active supernatant reduced the activity by 10%, 10 µM by 20%). In Table 13, the values are given in % of the control (SN-Medium) of the proliferation as effected by the mix-supernatants in 3 dilutions (1:4, 1:8, and 1:16).

TABLE 13

Proliferation of lymphoblastoid cell lines Raji CCL86 and Jurkat E6.1 after treatment with EA.hy936 endothelial cell culture supernatants (% of control ± s.d.)

|  | Jurket E6.1 | Raji CCL86 |
|---|---|---|
| SN-2417 (1 µM) | 52 ± 2** | 36 ± 6*** |
| SN-[2417 (1 µM) + 2418 (0.01 µM)] | 74 ± 4** | 57 ± 1*** |
| SN-[2417 (1 µM) + 2418 (0.1 µM)] | 88 ± 3* | 73 ± 3** |
| SN-[2417 (1 µM) + 2418 (1 µM)] | 89 ± 19 | 85 ± 16 |
| SN-2418 (1 µM) | 104 ± 1 | 99 ± 5 |
| SN-2435 (1 µM) | 50 ± 2* | 32 ± 3*** |
| SN-[2435 (1 µM) + 2418 (0.01 µM)] | 78 ± 24 | 53 ± 4*** |
| SN-[2435 (1 µM) + 2418 (0.1 µM)] | 83 ± 16 | 67 ± 6** |
| SN-[2435 (1 µM) + 2418 (1 µM)] | 87 ± 23 | 82 ± 16 |
| SN-2418 (1 µM) | 113 ± 11 | 100 ± 5 |
| SN-Medium - control | 100 | 100 |

Comments:
SN-Medium = supernatant of endothelial cell culture in medium, diluted with medium in the ratio given
SN-2417 = supernatant of endothelial cell culture stimulated with the mixture of isomers of mitraphylline in medium for 7 days in the concentration given
SN-2418 = supernatant of endothelial cell culture stimulated with the mixture of isomers of rhynchophylline in medium for 7 days in the concentration given
SN-2435 = supernatant of endothelial cell culture stimulated with the mixture of isomers of pteropodine in medium for 7 days, diluted with medium in the ratio given
Significantly different from control (Student's t-test): *p < 0.01, p < 0.005, *p < 0.001; n = 6.

10. Alkaloids alone were added to lymphocytes to exclude the possibility of a direct effect. Endothelial cells were grown without alkaloids and the alkaloids were added to the supernatant in order to prove that stimulation of the cells by the alkaloids is necessary for the production and/or release of the factor. Both experiments showed that neither the alkaloids alone nor in combination with a supernatant of untreated endothelial cells exert an effect on the proliferation of lymphocytes. Thus it was shown that the pentacyclic isomers do not affect directly the proliferation but rather induce endothelial cells to produce and/or release a factor which influences the proliferation of lymphocytes. It is assumed that endothelial cells produce a similar factor even without stimulation because the supernatants of unstimulated cultures do influence the proliferation, although to a minor degree. A lower dosage of pentacyclic oxindole alkaloids (0.1 µM) did not induce the production and/or release of the factor anymore (Table 14). Supernatants of endothelial cell cultures stimulated with IMM-2414 (c=0.1 µM) for 7 days (SN-2414) and non-stimulated (SN-medium) were added to lymphoblastoid cell cultures in several concentrations. The proliferation of the transformed cells was measured by [$^3$]thymidine uptake (cpm=counts per minute) after 2 days.

TABLE 14

Proliferation (cpm after [$^3$H]thymidine uptake) of lymphoblastoid cell lines in medium RPMI-1640

| Stimulant (dilution) | Raji CCL86 | Jurkat E6.1 |
|---|---|---|
| Medium | 27617 | 42536 |
| IMM-2414 (0.1 µM) | 28708 | 42779 |
| and under the influence of EA.hy926 endothelial cell culture supernatants | | |
| SN-Medium (1:2) | 38556 | 35917 |
| SN-2414 (1:2) | 36397 | 35653 |
| SN-Medium (1:4) | 36227 | 38982 |
| SN-2414 (1:4) | 28558 | 34048 |
| SN-Medium (1:8) | 30785 | 40389 |
| SN-2414 (1:8) | 22661 | 39902 |

Comments:
Medium = RPMI-1640 completed as specified above
IMM-2414 = solution of standard mixture of pentacyclic alkaloids in medium
SN-Medium = supernatant of endothelial cell culture in medium, diluted with medium in the ratio given
SN-2414 = supernatant of endothelial cell culture stimulated with the standard mixture of pentacyclic alkaloids in medium for 7 days, diluted with medium in the ratio given It can be seen that the alkaloids alone do not have an effect compared to the blank medium. The supernatants of low concentration-stimulated endothelial cell cultures (SN-2414) exhibit only a weak influence on the proliferation of the Raji and Jurkat cells. The proliferation-regulating factor binds to interferon-β-antiserum (from sheep) and can be isolated on sepharose.

As the factor enhances the proliferation of normal B and T lymphocytes, it is assumed that it also increases the release of other factors which are normally produced by lymphocytes, e.g. interferon-γ, various interleukins or a granulocyte-macrophage-stimulating-factor. Even if the activity of the factor is controlled by immunological regulatory circuits, it can be useful to limit this activity in a specific way. The tetracyclic alkaloids can be employed for this purpose because of their dose-dependent inhibition of the activity of the factor.

11. In addition, experiments were performed using simple derivatives of the pentacyclic alkaloids. From the mixture (IMM-2414) the corresponding carboxylic acids (IMM-2413) were prepared by alkaline hydrolysis, and alkaloid N-oxides (IMM-2433) by oxidation with hydrogen peroxide. Supernatants of endothelial cell cultures stimulated with IMM-2414, IMM-2413 or IMM-2433 for 7 days (SN-2414, SN-2413, SN-2433) and non-stimulated endothelial call cultures (SN-medium) were added to T lymphocyte cultures in several concentrations. It was demonstrated that the carboxylic acids had only weak activity and the N-oxides almost none (Table 15). Probably these derivatives, due to their higher polarity compared with the parent alkaloids, cannot enter the cells. It is also possible that the free amine and the methyl ester are essential pharmacophores.

TABLE 15

Proliferation (cpm after [³H]thymidine uptake) of human normal T lymphocytes in medium RPMI-1640

| Stimulant (dilution) | T lymphocytes |
|---|---|
| Medium | 1724 |
| IMM-2414 (1 µM) | 1309 |
| IMM-2413 (1 µM) | 876 |
| IMM-2433 (1 µM) | 1305 |
| and under the influence of EA.hy926 endothelial cell culture supernatants | |
| SN-Medium (1:4) | 2366 |
| SN-2414 (1:4) | 4864 |
| SN-2413 (1:4) | 2717 |
| SN-2433 (1:4) | 2418 |
| SN-Medium (1:8) | 2079 |
| SN-2414 (1:8) | 3103 |
| SN-2413 (1:8) | 2850 |
| SN-2433 (1:8) | 2327 |
| SN-Medium (1:16) | 2062 |
| SN-2414 (1:16) | 2493 |
| SN-2413 (1:16) | 2049 |
| SN-2433 (1:16) | 1994 |

Comments:
Medium = RPMI-1640 completed as specified above
IMM-2414 = solution of standard mixture of pentacyclic alkaloids in medium
IMM-2413 = solution of carboxylic acids prepared from the standard mixture of pentacyclic alkaloids in medium
IMM-2433 = solution of N-oxides prepared from from the standard mixture of pentacyclic alkaloids in medium
SN-Medium = supernatant of endothelial cell culture in medium, diluted with medium in the ratio given
SN-2414 = supernatant of endothelial cell culture stimulated with the standard mixture of pentacyclic alkaloids in medium for 7 days, diluted with medium in the ratio given
SN-2413 = supernatant of endothelial cell culture stimulated with the alkaloid carboxylic acids for 7 days, diluted with medium in the ratio given
SN-2433 = supernatant of endothelial cell culture stimulated with the alkaloid N-oxides for 7 days, diluted with medium in the ratio given.
All values result of single experiments.

It can be seen that the alkaloids alone do not have an effect compared to the blank medium. The supernatants of the non-stimulated endothelial cell cultures (SN-medium) already increase the proliferation, the supernatants of the IMM-2414-stimulated endothelial cell cultures (SN-2414) further enhance this effect. The supernatants of the IMM-2413-stimulated endothelial cell cultures (SN-2413) produce only weak effects, the supernatants of the IMM-2433-stimulated endothelial cell cultures (SN-2433) have no effect compared to supernatants of the non-stimulated endothelial cell cultures (SN-medium).

From these investigations and considerations it is seen that the composition of the mixture of isomers cannot be left to chance when a certain action on endothelial cells within a definite time is desired. Elimination from living organisms has to be considered. The different solubility of the isomers in water and lipids has also to be considered when a galenic form is developed. In order to obtain a specific induction of release of the factor the pentacyclic isomers have to be administered in proportions which are adjusted to the physiological equilibrium composition.

In general, RPMI-1640 was used as the culture medium for EA.hy926 endothelial cells and lymphocytes, completed with 10% fetal calf serum, 2 mM glutamin, 50 units/ml penicillin G and 50 µg/ml streptomycin. For HUVEC cultures HAM F12 was used, completed with 10% fetal calf serum, 60 µg/ml Endothelial Cell Growth Supplement and 100 µg/ml heparin. Supernatants of the endothelial cell cultures, stimulated with oxindole alkaloids for 7 days, were diluted with the medium and added to lymphocyte cultures in several concentrations. Proliferation of the lymphocytes was assayed by [³H]thymidine uptake. Thus, normal cells were treated with 1 µCi [³H]thymidine for 18 hours, and transformed cells were treated with 0.5 µCi [³H]thymidine for 5 hours. They were harvested on nitrocellulose, and radioactivity was measured in a scintillation counter. Every assay was performed in triplicate.

In vivo Experiments

An extract of Uncaria tomentosa root containing pentacyclic oxindole alkaloids was administered orally to rats and human volunteers, and the effect on the lymphocyte numbers was studied. The numbers of lymphocytes increased in patients with a suppressed immune system, whereas the lymphocyte count decreased in patients with a highly activated immune system.

EXAMPLES

1. Normal human umbilical vein endothelial cells (HUVEC, ATCC CRL-1730) are cultivated for 7 days at 37° C. in HAM F12 nutrient medium which was completed with 10% fetal calf serum, 60 µg/ml Endothelial Cell Growth Stimulant and 100 µg/ml heparin. Then the supernatant is taken, filtered sterile, diluted 1:4, and added to cultures of normal human T lymphocytes. The presence of the factor released from the endothelial cells leads within 5 days to an increase of the proliferation of the lymphocytes by 50%.

2. Transformed EA.hy926 endothelial cells are cultivated in RPMI-1640 nutrient medium which was completed with 10% fetal calf serum, 2 mM glutamine, 50 units/ml penicilline G, and 50 µg/ml streptomycin. Then the supernatant is taken, filtered sterile, diluted 1:4, and added to cultures of normal human B lymphocytes. The presence of the factor released from the endothelial cells leads within 5 days to an increase of the proliferation of the lymphocytes by 180%.

3. Normal human umbilical vein endothelial cells (HUVEC, ATCC CRL-1730) are cultivated for 7 days at 37° C. in HAM F12 nutrient medium which was completed with 10% fetal calf serum, 60 µg/ml Endothelial Cell Growth Stimulant, 100 µg/ml heparin, and which contains pentacyclic oxindole alkaloids (c=0.4 mg/l). Then the supernatant is taken, filtered sterile, diluted 1:4, and added to cultures of normal human T lymphocytes. The presence of the factor released from the endothelial cells leads within 5 days to an increase of the proliferation of the lymphocytes by 110%.

4. Transformed EA.hy926 endothelial cells are cultivated for 7 days in RPMI-1640 nutrient medium which was completed with 10% fetal calf serum, 2 mM glutamine, 50 units/ml penicilline G, 50 µg/ml streptomycin, and which contains pentacyclic oxindole alkaloids (c=0.4 mg/l). Then the supernatant is taken, filtered sterile, diluted 1:4, and added to cultures of normal human B lymphocytes. The presence of the factor released from the endothelial cells leads within 5 days to an increase of the proliferation of the lymphocytes by 330%.

5. Transformed EA.hy926 endothelial cells are cultivated for 7 days in RPMI-1640 nutrient medium which was completed with 10% fetal calf serum, 2 mM glutamine, 50 units/ml penicilline G, 50 µg/ml streptomycin, and which contains pteropodine and isopteropodine (c=0.4 mg/l). Then the supernatant is taken, filtered sterile, diluted 1:4, and added to cultures of leukemic Jurkat cells (ATCC E6.1). The presence of the factor released from the endothelial cells leads within 2 days to an inhibition of the proliferation of the lymphocytes by 80%

6. Transformed EA.hy926 endothelial cells are cultivated for 7 days in a nutrient medium which contains mitraphylline and isomitraphylline (c=0.4 mg/l). Then the supernatant is taken, filtered sterile, diluted 1:4, and added to cultures of highly activated T lymphocytes (lymphoblasts). The presence of the factor released from the endothelial cells leads within 2 days to an inhibition of the proliferation of the lymphocytes by 40%.

7. A dose of 1 g/kg bodyweight of an extract from the root of *Uncaria tomentosa* mod. pent. which contains approximately 1% pentacyclic oxindole alkaloids is administered orally to healthy rats. Within 28 days a significant (relative and absolute) lymphocytosis develops (in 5 male rats from 86.8% to 90.4%, from 8.4 G/l to 8.5 G/l in 5 female rats from 83.4% to 88.4%, from 4.9 G/l to 5.7 G/l).

8. A tumor patient whose lymphocyte count is diminished (relative and absolute lymphopenia, share of lymphocytes: 18% of leucocytes, 1.1 G/l) by chemotherapy (Taxol) is given an extract from the root of *Uncaria tomentosa* in a dose corresponding to 0.6 mg pentacyclic oxindole alkaloids daily. In spite of continued chemotherapy the lymphocyte counts rise significantly within 1 month (share of lymphocytes: 21% of leucocytes, 1.4 G/l).

9. A group of patients (n=30) with autoimmune disease received an extract from the root of *Uncaria tomentosa* corresponding to 0.6 mg pentacyclic oxindole alkaloids daily for one year. Initially, they had a mean total leucocyte count of 8.44 G/l (share of lymphocytes: 21.5%, 1.82 G/l). After half a year of treatment the leucocyte count was 8.66 G/l, the lymphocytes dropped to 18.2%, 1.57 G/l. After one year the leucocyte count was 8.50 G/l, and the lymphocytes remained stable at 18.5%, 1.57 G/l.

10. Transformed EA.hy926 endothelial cells are cultivated for 7 days at 37° C in a nutrient medium which contains mitraphylline and isomitraphylline (c=0.4 mg/l) or pteropodine and isopteropodine (c=0.4 mg/l). Then the supernatant is taken, filtered sterile, diluted (1:8, 1:16, 1:32) and added to cultures of normal human B lymphocytes. The supernatant which has been obtained from the mitraphylline-stimulated cells increases the proliferation of the lymphocytes by 260% in all dilutions, whereas the supernatant which has been obtained from the pteropodine-stimulated cells shows a dose-dependent activity (increase of proliferation by 250%, 170%, and 150%, respectively).

11. Normal human umbilical vein endothelial cells (HUVEC, ATCC CRL-1730) are cultivated for 7 days at 37° C. in HAM F12 nutrient medium which was completed with 10% fetal calf serum, 60 µg/ml Endothelial Cell Growth Stimulant, 100 µg/ml heparin, and which contains pentacyclic oxindole alkaloids (c=0.4 mg/l). Then the supernatant is taken and filtered sterile. 50 pi interferon-p-antiserum (from sheep) in sterile water (c=19000 units/ml) is added per ml of supernatant. The mixture is shaken and incubated for 1 hour at 4° C. Then 25 µl of a 10% protein-β-sepharose suspension is added, incubated for 30 minutes at 4° C. and centrifuged at 2000 g. From the sediment the factor-antiserum-complex is eluted with a 0.1 M solution of glycin hydrochloride at pH 2.6.

12. Extracts from the root of *Uncaria tomentosa* are tested for the absence of tetracyclic oxindole alkaloids by High Performance Liquid Chromatography (HPLC). A RP-18 (5 µm) column (125×4 mm) is used. A mixture of acetonitrile and 0.01 M phosphate buffer pH 7 (40:60) at a flow of 13 ml/min is used as the eluent at 52° C. A relable separation of tetracyclic and pentacyclic oxindole alkaloids is achieved. Detection is carried out at 247 nm. Only extracts which contain solely pentacyclic oxindole alkaloids are further processed.

Although endothelial cells are not part of the immune system, they possess the ability to release soluble factors into their environment which affect the behaviour of immune-related cells. It is the object of the present invention to effect the release of such a factor which increases the proliferation of resting or weakly activated lymphocytes and decreases the proliferation of highly activated lymphocytes and transformed lymphoblasts without reducing their viability. It is a further object of this invention to effect the release of this factor by stimulating endothelial cells with pentacyclic oxindole alkaloids. It is yet another object of this invention to limit the release of this factor by the simultaneous administration of tetracyclic oxindole alkaloids which act as antagonists. The production and use of this new proliferation-regulating factor are claimed.

We claim:

1. A preparation comprising a combination of mitraphylline and isomitraphylline, wherein said mitraphylline and isomitraphylline are pentacyclic oxindole alkaloids contained in an extract from *Uncaria tomentosa (Willd.)* dissolvable in a watery medium, said pentacyclic oxindole alkaloids dissolved in a watery medium in vitro being able to stimulate endothelial cells cultivated in a nutrient medium to release a lymphocyte proliferation regulating growth-factor into said nutrient medium.

2. The preparation of claim 1 further comprising a combination of pteropodine isopteropodine, speciophylline, and uncarine F, wherein said pteropodine, said isopteropodine, said speciophylline, and said uncarine F are pentacyclic oxindole alkaloids.

3. A preparation comprising a combination of mitraphylline and isomitraphylline, wherein said mitraphylline and said isomitraphylline are pentacyclic oxindole alkaloids contained in an extract from *Uncaria tomentosa (Willd.)* DC, inducing a release of a growth-factor from endothelial cells in vivo, which growth-factor increases the proliferation of resting or weakly activated B- and T-lymphocytes and decreases the proliferation of highly activated B- and T-lymphocytes as well as of transformed lymphoblasts, wherein when dissolved a watery medium, said pentacyclic oxindole alkaloids are able to stimulate in vitro and endothelial cells cultivated in a nutrient medium to release said growth-factor into said nutrient medium.

4. The preparation of claim 3 further comprising a combination of pteropodine, isopteropodine, speciophylline, and uncarine F, wherein said pteropodine, said isopteropodine, said speciophylline, and said uncarine F are pentacyclic oxindole alkaloids.

5. The preparation of claim 3 wherein said endothelial cells are present in a human subject.

6. The preparation of claim 4 wherein said endothelial cells are present in a human subject.

7. A preparation comprising a combination of mitraphylline and isomitraphylline, wherein said mitraphylline and said isomitraphylline are pentacyclic oxindole alkaloids contained in an extract from *Uncaria tomentosa* (*Willd.*) DC, inducing a release of growth-factor from endothelial cells in vitro, which growth-factor increases the proliferation of resting or weakly activated B- and T-lymphocytes and decreases the proliferation of highly activated B- and T-lymphocytes as well as transformed lymphoblasts, said preparation being dissolved in a watery medium.

8. The preparation of claim 7 further comprising a combination of pteropodine, isopteropodine, speciophylline and uncarine F, wherein said ptropodine, said isopteropodine, said speciophylline, and said uncarine F are pentacyclic oxindole alkaloids.

\* \* \* \* \*

UNITED STATES PATENT AND TRADEMARK OFFICE
CERTIFICATE OF CORRECTION

PATENT NO. : 7,238,374 B2
APPLICATION NO. : 09/788888
DATED : July 3, 2007
INVENTOR(S) : Klaus Keplinger et al.

It is certified that error appears in the above-identified patent and that said Letters Patent is hereby corrected as shown below:

Title Page, add

--(30) Foreign Application Priority Data

Jan. 20, 1997 (A) ……………………….. 73/97--

Column 18,

Line 5, "wherein said ptropodine," should read -- wherein said pteropodine, --

Line 18, "when dissolved a watery" should read -- when dissolved in a watery --

Line 58, "stimulate in vitro and endothelial" should read --stimulate in vitro endothelial --

Signed and Sealed this

Twenty-eighth Day of August, 2007

JON W. DUDAS
*Director of the United States Patent and Trademark Office*